US010172923B2

(12) United States Patent
Feghali-Bostwick et al.

(10) Patent No.: US 10,172,923 B2
(45) Date of Patent: *Jan. 8, 2019

(54) USE OF ENDOSTATIN PEPTIDES FOR THE TREATMENT OF FIBROSIS

(71) Applicant: University of Pittsburgh—Of the Commonwealth System of Higher Education, Pittsburgh, PA (US)

(72) Inventors: Carol A. Feghali-Bostwick, Mt Pleasant, SC (US); Yukie Yamaguchi, Kanagawa (JP)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/385,705

(22) Filed: Dec. 20, 2016

(65) Prior Publication Data

US 2017/0157217 A1 Jun. 8, 2017

Related U.S. Application Data

(60) Continuation of application No. 15/152,468, filed on May 11, 2016, now Pat. No. 9,556,252, which is a division of application No. 14/207,246, filed on Mar. 12, 2014, now Pat. No. 9,365,616, which is a continuation of application No. 13/939,058, filed on Jul. 10, 2013, now Pat. No. 8,716,232, which is a division of application No. 13/503,339, filed as application No. PCT/US2010/053831 on Oct. 22, 2010, now Pat. No. 8,507,441.

(60) Provisional application No. 61/261,280, filed on Nov. 13, 2009, provisional application No. 61/254,143, filed on Oct. 22, 2009.

(51) Int. Cl.
| | |
|---|---|
| *A61K 38/00* | (2006.01) |
| *A61P 17/00* | (2006.01) |
| *A61K 38/08* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07H 21/04* | (2006.01) |
| *A61K 38/39* | (2006.01) |
| *C07K 14/78* | (2006.01) |
| *C07K 14/47* | (2006.01) |
| *C07K 7/06* | (2006.01) |

(52) U.S. Cl.
CPC ............ *A61K 38/39* (2013.01); *A61K 38/08* (2013.01); *C07K 7/06* (2013.01); *C07K 14/47* (2013.01); *C07K 14/78* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,764,955 B2 | 7/2004 | O'Reilly et al. | |
| 9,365,616 B2 * | 6/2016 | Feghali-Bostwick | ........................ C07K 14/78 |
| 2006/0193830 A1 | 8/2006 | Hauswirth et al. | |

FOREIGN PATENT DOCUMENTS

| | | | |
|---|---|---|---|
| EP | 1 985 302 | 10/2008 | |
| JP | 2007084459 A * | 4/2007 | |
| JP | 2007084459 A | 4/2007 | |
| KR | 10-2000-0006175 | 9/2001 | |
| WO | WO 2000/067771 | 11/2000 | |
| WO | WO 2002/068457 | 9/2002 | |
| WO | WO-2005021756 A1 * | 3/2005 | ............ A61K 38/10 |
| WO | WO 2008/014564 | 2/2008 | |

OTHER PUBLICATIONS

Anonymous "Fragment Crystallizable Region," http://en.wikipedia.org.wiki/Fragement_crystallizable_region (published Dec. 10, 2007).
Chufán et al., "Amidation of Bioactive Peptides: The Structure of the Lyase Domain of the Amidating Enzyme," *Structure* 17:965-973 (Jul. 15, 2009).
Hui et al., "Effect of Recombinant Adenovirus Vector Expressing Human Endostatin on Endothelial Cell Proliferation," *Journal of Clinical Rehabilitative Tissue Engineering Research* 12(50): 9986-9989 (Dec. 9, 2008).
International Search Report from parent PCT Application No. PCT/US2010/53831, 8 pages, (dated Jan. 7, 2011).
Isobe et al., "Inhibition of Endostatin/Collagen XVIII Deteriorates Left Ventricular Remodeling and Heart Failure in Rat Myocardial Infarction Model," *Circulation Journal* 74: 109-119 (Jan. 2010).
Kim and Seong, "Peptide Amidation: Production of Peptide Hormones in vivo and in vitro," *Biotechnol Bioprocess Engineering* 6:244-251 (Aug. 2001).

(Continued)

*Primary Examiner* — James H Alstrum-Acevedo
*Assistant Examiner* — Zachary J Miknis
(74) *Attorney, Agent, or Firm* — Klarquist Sparkman, LLP

(57) ABSTRACT

C-terminal endostatin polypeptides are disclosed herein. Polynucleotides encoding these polypeptide, host cells transformed with the polynucleotides, and methods of using these polypeptides and polynucleotides are disclosed. Uses of these polypeptide, polynucleotides and expression vectors include the treatment of fibrosis in a subject. Thus, methods are provided for treating fibrosis, including fibrosis of the skin and/or the lung.

14 Claims, 17 Drawing Sheets

Specification includes a Sequence Listing.

(56) References Cited

OTHER PUBLICATIONS

Kim et al., "Endostatin Inhibits Endothelial and Tumor Cellular Invasion by Blocking the Activation and Catalytic Activity of Matrix Metalloproteinase 2," *Cancer Research* 60:5410-5413 (Oct. 1, 2000).
Larsson "Immunochemistry: Theory and Practice," CRC Press p. 1 (1988).
Lee et al., "Linking Antibody Fe Domain to Endostatin Significantly Improves Endostatin Half-life and Eq2fficacy," Clin. Cancer Res. 14(5): 1487-1493 (Mar. 1, 2008).
Morbidelli et al., "Angiosuppressive and Angiostimulatory Effects Exerted by Synthetic Partial Sequences of Endostatin," *Clinical Cancer Research* 9: 5358-5369 (Nov. 12, 2003).
Richter et al., "Soluble Endostatin is a Novel Inhibitor of Epithelial Repair in Idiopathic Pulmonary Fibrosis," *Thorax* 64:156-161 (2009).
Rodriguez et al., "Lysyl Oxidase as a Potential Therapeutic Target," *Drug News Perspect* 21(4): 218-224 (2008).
Szauter et al., "Lysyl Oxidase in Development, Aging and Pathologies of the Skin," *Pathologie Biologie* 53: 448-456 (2005).
Written Opinion from parent PCT Application No. PCT/US2010/53831, 8 pages, (dated Jan. 7, 2011).
Yamaguchi et al., "Endostatin Inhibits VEGF-induced Endothelial Cell Migration and Tumor Growth Independently of Zinc Binding," *EMBO* 18:4414-4423 (Aug. 16, 1999).

\* cited by examiner

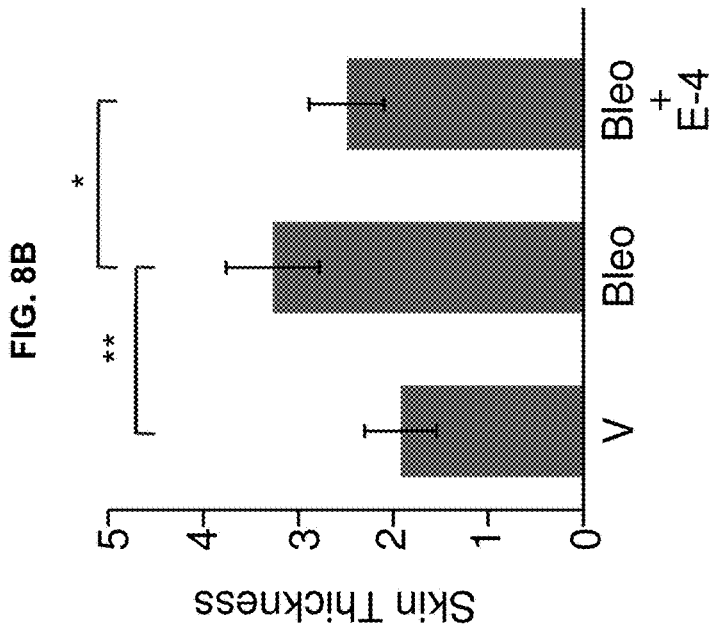
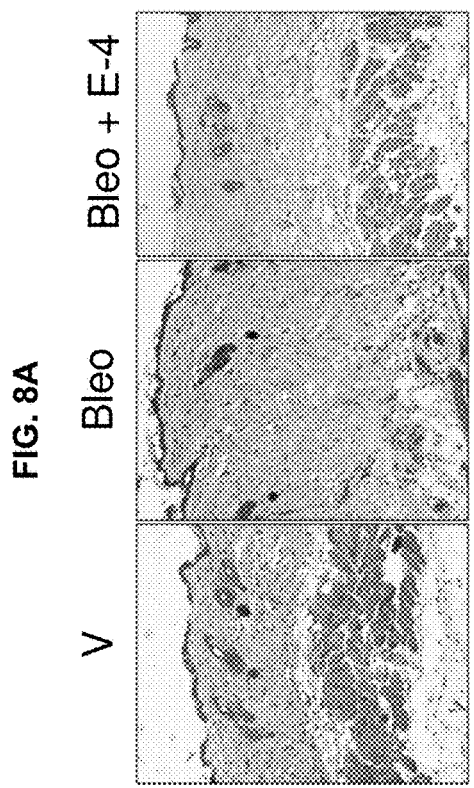

FIG. 9
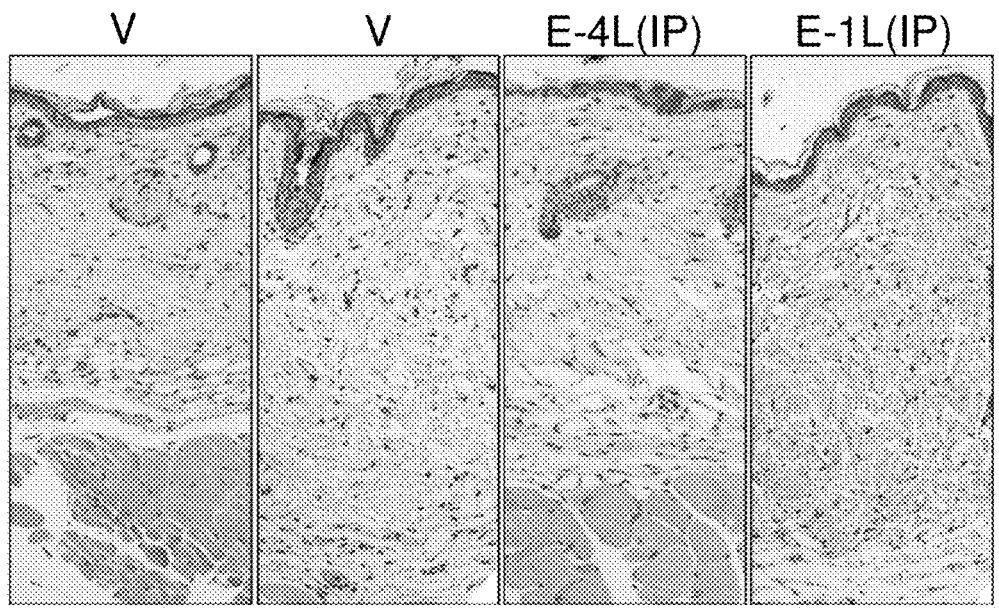
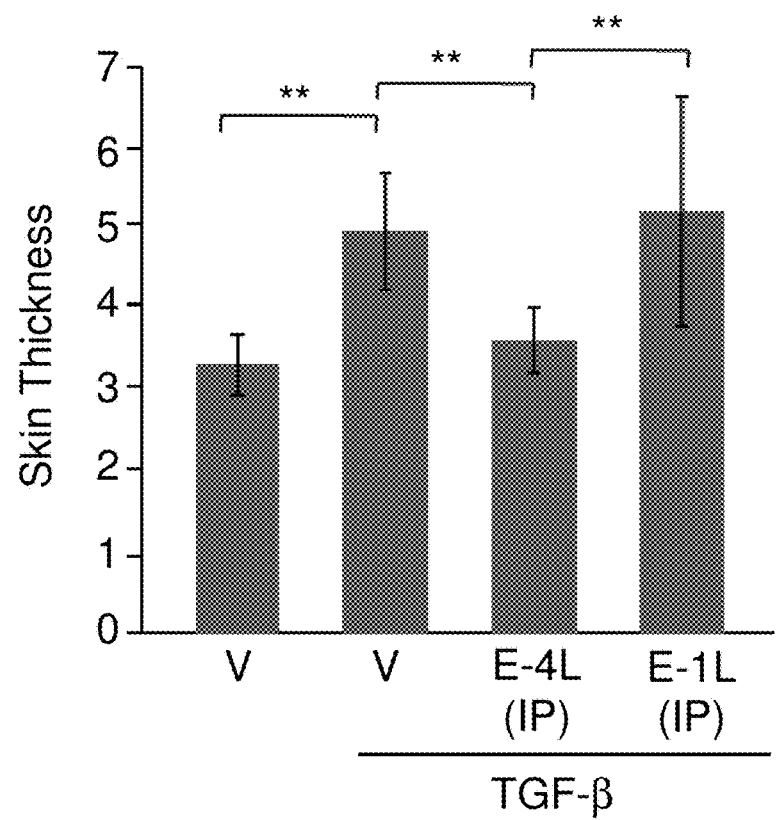

FIG. 10C
C Trichrome
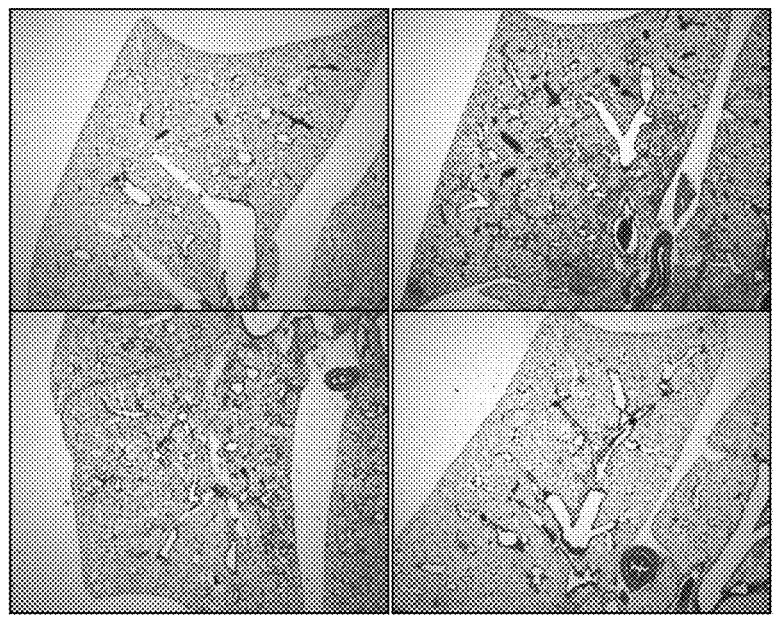
H&E
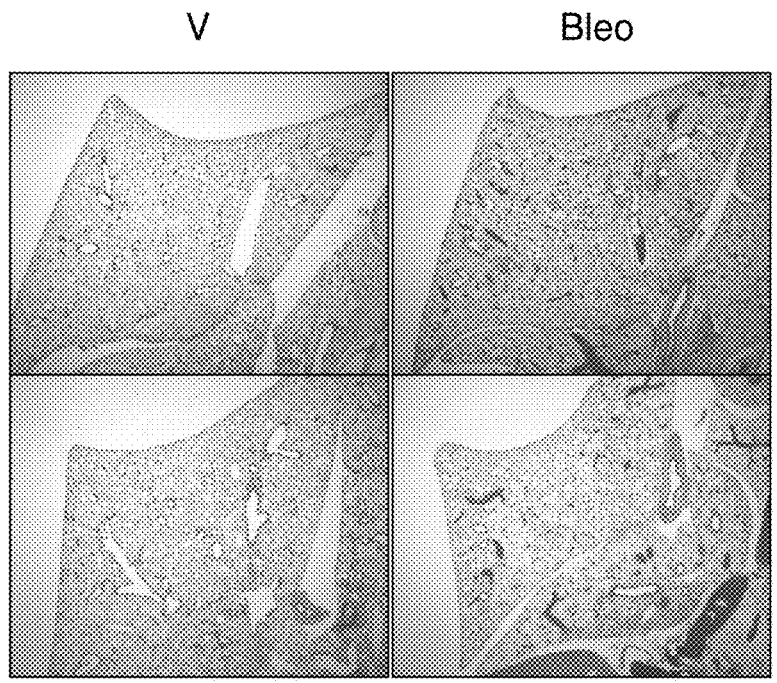

Pro-MMP2
Active-MMP2

FIG. 15
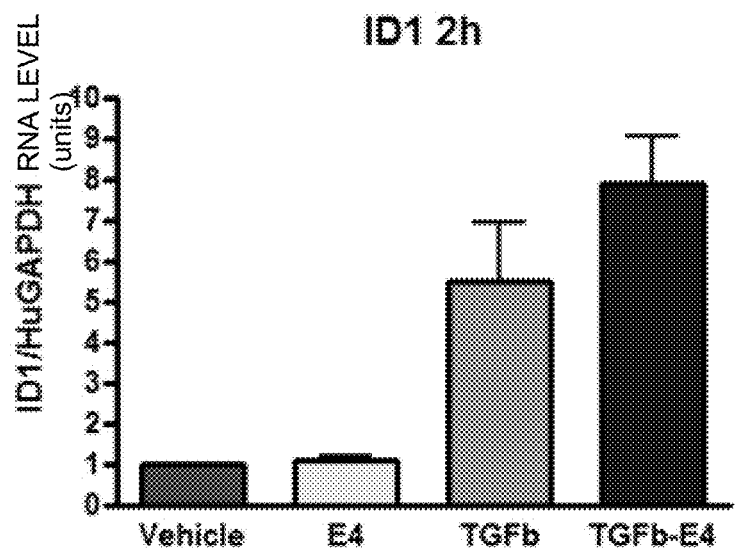
FIG. 16
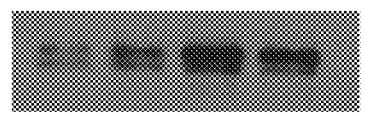
Egr 1
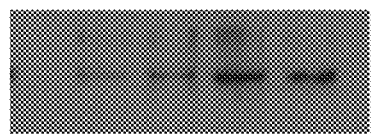
Collagen I
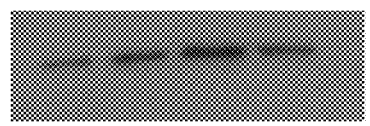
α SMA
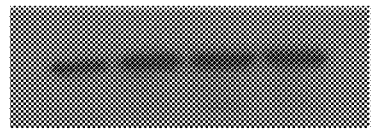
α Tubulin

SEQUENCE LISTING

```
<160> NUMBER OF SEQ ID NOS: 13

<210> SEQ ID NO 1
<211> LENGTH: 555
<212> TYPE: DNA
<213> ORGANISM: Homo sapiens

<400> SEQUENCE: 1
atgcacagcc accgcgactt ccagccggtg ctccacctgg ttgcgctcaa cagcccctg      60 tcaggcggca tgcggggcat ccgcggggcc gacttccagt gcttccagca ggcgcgggcc    120
gtggggctgg cgggcacctt ccgcgccttc ctgtcctcgc gcctgcagga cctgtacagc    180
atcgtgcgcc gtgccgaccg cgcagccgtg cccatcgtca acctcaagga cgagctgctg    240
tttcccagct gggaggctct gttctcaggc tctgagggtc cgctgaagcc cggggcacgc    300
atcttctcct ttaacggcaa ggacgtcctg acccacccca cctggcccca gaagagcgtg    360
tggcatggct cggaccccaa cgggcgcagg ctgaccgaga gctactgtga cgtggcgg     420 acggaggctc cctcggccac gggccaggcc tactcgctgc tgggggggcag gctcctgggg    480 cagagtgccg cgagctgcca tcacgcctac atcgtgctat gcattgagaa cagcttcatg    540
actgcctcca agtag                                                      555

<210> SEQ ID NO 2
<211> LENGTH: 183
<212> TYPE: PRT
<213> ORGANISM: Homo sapiens

<400> SEQUENCE: 2

His Ser His Arg Asp Phe Gln Pro Val Leu His Leu Val Ala Leu Asn
1               5                  10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45
```

```
Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asn Gly Lys Asp Val Leu Thr His Pro
                100                 105                 110

Thr Trp Pro Gln Lys Ser Val Trp His Gly Ser Asp Pro Asn Gly Arg
            115                 120                 125

Arg Leu Thr Glu Ser Tyr Cys Glu Thr Trp Arg Thr Glu Ala Pro Ser
    130                 135                 140

Ala Thr Gly Gln Ala Tyr Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 3
<211> LENGTH: 552
<212> TYPE: DNA
<213> ORGANISM: Mus musculus

<400> SEQUENCE: 3
catactcatc aggactttca gccagtgctc cacctggtgg cactgaacac ccccctgtct      60
ggaggcatgc gtggtatccg tggagcagat ttccagtgct ccagcaagc ccgagccgtg     120 gggctgtcgg gcaccttccg ggcttttcctg tcctctaggc tgcaggatct ctatagcatc    180
gtgcgccgtg ctgaccgggg gtctgtgccc atcgtcaacc tgaaggacga ggtgctatct    240
cccagctggg actccctgtt ttctggctcc cagggtcaac tgcaacccgg ggcccgcatc    300
ttttcttttg acggcagaga tgtcctgaga cacccagcct ggccgcagaa gagcgtatgg    360
cacggctcgg accccagtgg gcggaggctg atggagagtt actgtgagac atggcgaact    420
gaaactactg ggctacagg tcaggcctcc tccctgctgt caggcaggct cctggaacag    480
aaagctgcga gctgccacaa cagctacatc gtcctgtgca ttgagaatag cttcatgacc    540
tctttctcca aa                                                        552

<210> SEQ ID NO 4
<211> LENGTH: 184
<212> TYPE: PRT
<213> ORGANISM: Mus musculus

<400> SEQUENCE: 4

His Thr His Gln Asp Phe Gln Pro Val Leu His Leu Val Ala Leu Asn
1               5                   10                  15

Thr Pro Leu Ser Gly Gly Met Arg Gly Ile Arg Gly Ala Asp Phe Gln
                20                  25                  30

Cys Phe Gln Gln Ala Arg Ala Val Gly Leu Ser Gly Thr Phe Arg Ala
            35                  40                  45

Phe Leu Ser Ser Arg Leu Gln Asp Leu Tyr Ser Ile Val Arg Arg Ala
    50                  55                  60

Asp Arg Gly Ser Val Pro Ile Val Asn Leu Lys Asp Glu Val Leu Ser
65                  70                  75                  80
```

```
Pro Ser Trp Asp Ser Leu Phe Ser Gly Ser Gln Gly Gln Leu Gln Pro
                 85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
    130                 135                 140

Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
                180
```

```
<210> SEQ ID NO 5
<211> LENGTH: 699
<212> TYPE: DNA
<213> ORGANISM: Homo sapiens

<400> SEQUENCE: 5
gagcccaaat cttgtgacaa aactcacaca tgcccaccgt gcccagcacc tgaactcctg      60
gggggaccgt cagtcttcct cttccccccca aaacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga caactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaatga                            699
```

```
<210> SEQ ID NO 6
<211> LENGTH: 244
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gly
65                  70                  75                  80

Ile Asn Tyr Asn Ser Thr Tyr Arg Val Val Ser Val Leu Thr Val Leu
                85                  90                  95
```

His Gly Ile Asn Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gly Ile Asn Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gly Ile Asn Pro Glu Asn Asn Tyr Lys Thr Thr Pro Pro Val Leu Asp
            180                 185                 190

Ser Asp Gly Ser Phe Phe Leu Tyr Ser Lys Leu Thr Val Asp Lys Ser
        195                 200                 205

Arg Trp Gln Gly Ile Asn Gly Asn Val Phe Ser Cys Ser Val Met His
    210                 215                 220

Glu Ala Leu His Asn His Tyr Thr Gly Ile Asn Lys Ser Leu Ser Leu
225                 230                 235                 240

Ser Pro Gly Lys

<210> SEQ ID NO 7
<211> LENGTH: 48
<212> TYPE: DNA
<213> ORGANISM: Homo sapiens

<400> SEQUENCE: 7
tctagaggtg gtctagtgcc gcgcggcagc ggttccccg ggttgcag                    48

<210> SEQ ID NO 8
<211> LENGTH: 16
<212> TYPE: PRT
<213> ORGANISM: Homo sapiens

<400> SEQUENCE: 8

Ser Arg Gly Gly Leu Val Pro Arg Gly Ser Gly Ser Pro Gly Leu Gln
1               5                   10                  15

<210> SEQ ID NO 9
<211> LENGTH: 48
<212> TYPE: PRT
<213> ORGANISM: Rattus rattus

<400> SEQUENCE: 9

Ser Tyr Cys Glu Thr Trp Arg Thr Glu Ala Thr Gly Val Thr Gly Gln
1               5                   10                  15

Ala Ser Ser Leu Leu Ser Gly Arg Leu Leu Glu Gln Lys Ala Glu Ser
            20                  25                  30

Cys His Asn Ser Tyr Ile Val Leu Cys Ile Glu Asn Ser Phe Met Thr
        35                  40                  45

<210> SEQ ID NO 10
<211> LENGTH: 48
<212> TYPE: PRT
<213> ORGANISM: Bos taurus

<400> SEQUENCE: 10

Ser Tyr Cys Glu Thr Trp Arg Thr Asp Ser Arg Ala Ala Thr Gly Gln
1               5                   10                  15

Ala Ser Ser Leu Leu Ala Gly Arg Leu Leu Glu Gln Lys Ala Ala Gly

```
            20                  25                  30
Cys His Asn Ala Phe Ile Val Leu Cys Ile Glu Asn Ser Phe Met Thr
        35                  40                  45

<210> SEQ ID NO 11
<211> LENGTH: 48
<212> TYPE: PRT
<213> ORGANISM: Homo sapiens

<400> SEQUENCE: 11

Asn Tyr Cys Glu Ala Trp Arg Thr Ala Asp Thr Ala Val Thr Gly Leu
1               5                  10                  15

Ala Ser Pro Leu Ser Thr Gly Lys Ile Leu Asp Gln Lys Ala Tyr Ser
            20                  25                  30

Cys Ala Asn Arg Leu Ile Val Leu Cys Ile Glu Asn Ser Phe Met Thr
        35                  40                  45

<210> SEQ ID NO 12
<211> LENGTH: 552
<212> TYPE: DNA
<213> ORGANISM: Homo sapiens

<400> SEQUENCE: 12
cacagccacc gcgacttcca gccggtgctc cacctggttg cgctcaacag cccccctgtca    60 ggcggcatgc gggcatccg cggggccgac ttccagtgct ccagcaggc gcgggccgtg      120 gggctggcgg gcaccttccg cgccttcctg tcctcgcgcc tgcaggacct gtacagcatc    180
gtgcgccgtg ccgaccgcgc agccgtgccc atcgtcaacc tcaaggacga gctgctgttt    240
cccagctggg aggctctgtt ctcaggctct gagggtccgc tgaagcccgg ggcacgcatc    300
ttctcctttg acggcaagga cgtcctgagg cacccccacct ggccccagaa gagcgtgtgg    360
catggctcgg accccaacgg gcgcaggctg accgagagct actgtgagac gtggcggacg    420
gaggctccct cggccacggg ccaggcctcc tcgctgctgg ggggcaggct cctggggcag    480
agtgccgcga gctgccatca cgcctacatc gtgctctgca ttgagaacag cttcatgact    540
gcctccaagt ag                                                         552

<210> SEQ ID NO 13
<211> LENGTH: 183
<212> TYPE: PRT
<213> ORGANISM: Homo sapiens

<400> SEQUENCE: 13

His Ser His Arg Asp Phe Gln Pro Val Leu His Leu Val Ala Leu Asn
1               5                  10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110
```

-continued

```
Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180
```

USE OF ENDOSTATIN PEPTIDES FOR THE TREATMENT OF FIBROSIS

CROSS REFERENCE TO RELATED APPLICATION

This is a continuation of U.S. patent application Ser. No. 15/152,468, filed on May 11, 2016, which is divisional of U.S. patent application Ser. No. 14/207,246, filed Mar. 12, 2014, issued as U.S. Pat. No. 9,365,616, which is a continuation of U.S. patent application Ser. No. 13/939,058, filed Jul. 10, 2013, issued as U.S. Pat. No. 8,716,232, which is a divisional of U.S. patent application Ser. No. 13/503,339, filed Apr. 20, 2012, issued as U.S. Pat. No. 8,507,441, which is the U.S. national stage of PCT Application No. PCT/US2010/053831, filed Oct. 22, 2010, which was published in English under PCT Article 21(2), which claims the benefit of U.S. Provisional Application No. 61/261,280, filed Nov. 13, 2009 and U.S. Provisional Application No. 61/254,143, filed Oct. 22, 2009. The prior applications all are incorporated by reference herein in their entirety.

STATEMENT OF GOVERNMENT SUPPORT

This invention was made with government support under grant AR050840 awarded by the National Institutes of Health; the government has certain rights in the invention.

FIELD

This relates to the field of fibrosis, specifically to the use of C-terminal polypeptides of endostatin for the treatment of fibrosis.

BACKGROUND

Endostatin, a 183 amino acid proteolytic cleavage fragment corresponding to the C-terminus of collagen 18, has anti-tumor activity with no toxic side effects (O'Reilly et al. (1997) Cell, 88: 277-285.; Kisker et al. (2001) Cancer Res, 61:7669-7674; Dhanabal et al. (1999) Cancer Res, 59: 189-197; Yoon et al. (1999) Cancer Res, 59: 6251-6256; Folkman and Kalluri, (2003) Cancer Medicine, 6th edition, pp. 161-194. Hamilton: B. C. Decker Inc.). A number of anti-angiogenic activities have been reported for this protein, such as inhibition of endothelial cell proliferation, migration, and tube formation. This activity has been localized to the N-terminal region of endostatin. Endostatin also suppresses vascular endothelial growth factor (VEGF)-induced vascular permeability (Takahashi et al. (2003) Faseb J, 17: 896-898). Endostatin inhibits endothelial cell migration by inhibiting phosphorylation of focal adhesion kinase via binding to α5β1 integrin (Wickstrom et al. (2002) Cancer Res, 62: 5580-5589). It also has been shown that cell surface glypicans are low-affinity endostatin receptors (Karumanchi et al. (2001) Mol Cell, 7: 811-822). Endostatin has been implicated in several signaling pathways, such as downregulation of c-myc (Shichiri and Hirata (2001) Faseb J, 15: 1044-1053), cyclin-D1 (Hanai et al. (2002) J Biol Chem, 277. 16464-16469) and RhoA activity (Wickstrom et al. (2003) J Biol Chem, 278: 37895-37901), blockage of VEGF signaling (Hajitou et al. (2002) Faseb J, 16: 1802-1804; Kim et al. (2002) J Biol Chem, 277: 27872-27879), and inhibition of the wnt-signaling pathway (Hanai et al. (2002) J Cell Biol, 158: 529-539). Furthermore, endostatin has been shown to bind and inactivate metalloproteinases (Kim et al. (2000) Cancer Res, 60: 5410-5413; Nyberg et al. (2003) J Biol Chem, 278: 22404-22411; Lee et al. (2002) FEBS Lett, 519: 147-152) and to regulate a spectrum of genes which suppress angiogenesis (Abdollahi et al. (2004) Mol Cell, 13: 649-663).

The crystal structures of both murine and human endostatin have been resolved (Hohenester et al. (1998) Embo J, 17: 1656-1664; Ding et al. (1998) Proc Natl Acad Sci USA, 95: 10443-10448) and show a noncovalently held dimer at high concentration required for crystallization (Ding et al. (1998) Proc Natl Acad Sci USA, 95: 10443-10448). The presence of two disulfide bonds results in a highly folded structure. Endostatin binds one atom of zinc per monomer via the three histidines in the N-terminus of the molecule (histidines 1, 3, and 11) and asparatic 76. The heparin binding property of endostatin is mediated by noncontiguous arginines clustered over the three dimensional globular surface of the molecule (Sasaki et al. (1999) Embo J, 18: 6240-6248).

Excessive deposition of extra cellular matrix (ECM) components such as fibronectin (FN) and type I collagen (Col1α1) by organ fibroblasts is defined as fibrosis. Organ fibrosis is the final common pathway for many diseases that result in end-stage organ failure. However, effective therapy for organ fibrosis is still unavailable (see, for example, Bjoraker et al., Am. J. Respir. Crit. Care. Med 2000; 157:199-203). Uncontrollable wound-healing responses, including acute and chronic inflammation, angiogenesis, activation of resident cells, and ECM remodeling, are thought to be involved in the pathogenesis of fibrosis (Wynn, J Clin Invest 2007; 117:524-29; Kalluri et al., Curr Opin Nephrol Hypertens 2000; 9:413-8). TGF-β is the prototype fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs) (see, for example, Branton et al., Microbes Infect 1999; 1:1349-65). Despite high expectations, a clinical trial of a monoclonal anti-TGF-β antibody in patients with early SSc failed to show any efficacy (Varga et al., Nature Reviews Rheumatology 2009; 5:200-6). Thus, a need remains for other treatments of fibrosis.

SUMMARY

C-terminal endostatin polypeptides are disclosed herein that have anti-fibrotic activity. In some embodiments, these polypeptides include, consist essentially of or consist of (1) at least 40 consecutive amino acids of the amino acid sequence set forth as amino acids 133-180 of SEQ ID NO: 2, SEQ ID NO: 13 or SEQ ID NO: 4; (2) at least 40 consecutive amino acids of the amino acid sequence set forth as amino acids 133-180 of SEQ ID NO: 2, SEQ ID NO: 13 or SEQ ID NO: 4, with at most 5 amino acid substitutions, (3) the amino acid sequence set forth as amino acids 133-180 of SEQ ID NO: 2, SEQ ID NO: 13 or SEQ ID NO: 4; or (4) the amino acid sequence set forth as amino acids 133-180 of SEQ ID NO: 2, SEQ ID NO: 13 or SEQ ID NO: 4 with at most 5 amino acid substitutions. These polypeptides have anti-fibrotic activity and do not include amino acids 1-92 of SEQ ID NO: 2, SEQ ID NO: 13, or SEQ ID NO: 4, respectively. Polynucleotides encoding these polypeptides, host cells transformed with the polynucleotides, and methods of using these polypeptides and polynucleotides are disclosed. In one example, the polypeptide includes a modification of the carboxy terminal polypeptide to include an amide.

In some embodiments, methods are disclosed for inhibiting fibrosis in vivo or in vitro. In additional embodiments, methods are disclosed for the treatment of fibrosis in a subject. In some specific non-limiting examples, the subject has scleroderma or pulmonary fibrosis.

The foregoing and other features and advantages will become more apparent from the following detailed description of several embodiments, which proceeds with reference to the accompanying figures.

BRIEF DESCRIPTION OF THE FIGURES

FIGS. 8A-8B. The effect of endostatin E-4 on bleomycin induced dermal fibrosis in vivo. A: Mice were injected subcutaneously with 1×PBS as vehicle (V) or Bleomycin (Bleo; 20 μg/mouse) daily. E-4 (10 μg/ml) was mixed with bleomycin on the first day, and daily bleomycin administration was continued without subsequent injections of E4 (Bleo+E-4). Skin was harvested after 10 days. Sections were stained with H&E. Magnification, 100×. B: Graphical summary of dermal thickness data shown in A. Data represent three independent experiments. Mann-Whitney U test was used for statistical analysis. * P<0.001, ** P<0.00001. E4 administration caused a significant attenuation of bleomycin induced dermal fibrosis even with a single administration of E4.

FIG. 9. E4 reverses TGF β-induced dermal fibrosis even if administered 3 days following TGF-β. Mouse skin was treated with TGF-β day 1 and E-4L or E-1L (this is E-4 and E-1 administered after a 3 day lag between administration of the fibrotic trigger and the administration of the peptide. E-1 or E-4 was administered intraperitoneally (IP) at day3 and harvested at day7. E4 caused a significant decrease of TGFbeta induced dermal fibrosis on day 7. Thus E4 prevents (FIGS. 4-6) and reverses (FIG. 9) dermal fibrosis triggered by TGFβ.

FIG. 10A-10C. E4 attenuates bleomycin induced lung fibrosis in vivo. A: Sixty μg of bleomycin was administrated intratracheally in combination with DMSO as a vehicle (Bleo) or E-4 (Bleo+E-4; 10 μg/ml). In some mice, E-4 (10 μg/ml) was administered intratracheally (IT) three days following bleomycin treatment (Bleo+E-4L). PBS was used as a vehicle for bleomycin (V). Lungs were harvested 10 days post-treatment. Representative images stained with H&E (left panel) and Masson trichrome (right panel) are representative of 3 independent experiments. Magnification, 100×. E4 administered concomitantly with bleomycin or three days following bleomycin caused a marked reduction in fibrosis and Masson Trichrome staining. B: Quantification of acid soluble collagen obtained from mouse lungs treated as in panel C with V, Bleo, Bleo+E-4, and Bleo+E-4L. The levels of collagen are presented as μg/mg (lung) from three independent experiments. Unpaired-t test was used for statistical analysis. * P<0.05. E4 polypeptide given 3 days after bleomycin significantly reduced collagen levels in mouse lungs C: Lower magnification (2×) of mouse lung shown in FIG. 9 (BLM+E4/E4L IT day10). For Bleo+E4L, Bleo was administered first, then there was a lag of three days between Bleo and E4 administration).

FIG. 15. E4 reduces fibrosis in vitro by inducing expression of ID1, an inhibitor of TGF β, in primary human lung fibroblasts. Real-time PCR analysis was performed to determine the ID1 mRNA levels under the indicated conditions.

FIG. 16. E-4 reduces fibrosis in vitro by reducing levels of the master transcription factor Egr-1 in primary human lung fibroblasts. Reduction of Egr-1 levels parallels that of collagen, SMA, and fibronectin. Lane 1: vehicle (DMSO); Lane 2: E4; Lane 3: TGFβ, Lane 4 TGFβ followed by E4 after 60 minutes. The samples were harvested after 24 hours.

SEQUENCE LISTING

Figure 1A:
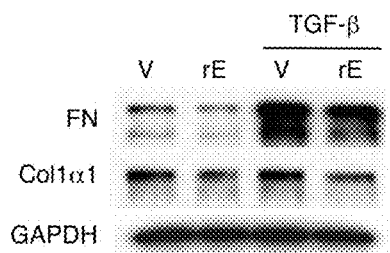
FIGS. 1A-1F. ECM production in recombinant endostatin- and endostatin-derived peptide-treated fibroblasts in combination with TGF-β stimulation. A: FN and Col1α1 expression in human normal lung fibroblasts (NL) treated with vehicle (V), rE alone, or both with prior TGF-β stimulation. Proteins were detected western blot. GAPDH was used as a loading control for lysates. B: FN and Col1α1 expression of endostatin polypeptide-treated lung fibroblasts following TGF-β stimulation in primary pulmonary fibroblasts from a healthy control, a patient with SSc, and a patient with IPF. C: Graphical summary of FN and Col1α1 expression in lung fibroblasts obtained using fibroblasts from 4 healthy controls (NL), 3 patients with SSc, and 3 patients with IPF. Intensity of bands was normalized to that of GAPDH and expressed as a ratio to Vehicle (V). Paired-t test was used for statistical analysis. * P<0.04, ** P<0.01. D: Representative result of FN and Col1α1 levels in human skin fibroblasts obtained from a patient with morphea and a patient with SSc. E: Representative result of FN and Col1α1 expression in fibrotic fibroblasts obtained from a patients with IPF treated with V, 5 μg/ml of rE, or endostatin polypeptides alone (left). IPF fibroblasts were treated with different concentrations (5, 10, and 20 μg/ml) of E4. DMSO (V) was added in a volume equivalent to that in the lane corresponding to 20 μg/ml of E4 (right). F: α-SMA levels in normal lung fibroblasts treated with endostatin polypeptides following TGF-β stimulation.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-84102-08_Sequence-_Listing.txt, Dec. 20, 2016, 12.6 KB], which is incorporated by reference herein. In the accompanying sequence listing:

SEQ ID NO: 1 is an exemplary nucleic acid sequence encoding human endostatin.

SEQ ID NO: 2 is the amino acid sequence of human endostatin.

SEQ ID NO: 3 is an exemplary nucleic acid sequence encoding mouse endostatin.

SEQ ID NO: 4 is the amino acid sequence of mouse endostatin.

SEQ ID NO: 5 is an exemplary nucleic acid sequence encoding a human immunoglobulin (Ig)G$_1$ protein.

SEQ ID NO: 6 is the amino acid sequence of a human IgG$_1$ protein.

SEQ ID NO: 7 is an exemplary nucleic acid sequence encoding a linker.

SEQ ID NO: 8 is an amino acid sequence of a linker.

SEQ ID NO: 9 is a portion of the rat endostatin polypeptide.

SEQ ID NO: 10 is a portion of the cow endostatin polypeptide.

SEQ ID NO: 11 is a portion of the human collagen XV polypeptide.

SEQ ID NO: 12 is an exemplary nucleic acid sequence encoding an endostatin.

SEQ ID NO: 13 is an amino acid sequence of an exemplary amino acid sequence of endostatin that differs from SEQ ID NO: 2 by three amino acid substitutions.

DETAILED DESCRIPTION

C-terminal endostatin polypeptides are disclosed herein. In some embodiments, these polypeptides include, consist essentially of, or consist of (1) at least 40 consecutive amino acids of the amino acid sequence set forth as amino acids 133-180 of SEQ ID NO: 13 or SEQ ID NO: 2; (2) at least 40 consecutive amino acids of the amino acid sequence set forth as amino acids 133-180 of SEQ ID NO: 13 or SEQ ID NO: 2, with at most 5 amino acid substitutions, (3) the amino acid sequence set forth as amino acids 133-180 of SEQ ID NO: 13 or SEQ ID NO: 2; or (4) the amino acid sequence set forth as amino acids 133-180 of SEQ ID NO: 13 or SEQ ID NO: 2 with at most 5 amino acid substitutions; wherein the polypeptide has anti-fibrotic activity and wherein the polypeptide does not comprise amino acids 1-92 of SEQ ID NO: 13 or SEQ ID NO: 2. In some embodiments, the polypeptide is amidated at the C-terminus. Polynucleotides encoding these polypeptides, host cells transformed with the polynucleotides, and methods of using these polypeptides and polynucleotides are disclosed. These methods include the treatment of fibrosis in a subject. For example, methods are provided for treating fibrotic conditions of the lung and the skin. In some embodiments, the anti-fibrotic C-terminal endostatin polypeptides disclosed herein can selectively inhibiting fribrosis. In some examples, fibrosis is inhibited without inhibiting angiogenesis. Thus, the C-terminal endostatin polypeptides can be used to more specifically and selectively target unwanted fibrosis, without interfering with angiogenesis, to achieve a desired therapeutic outcome.

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Amidation or amide derivative: A post-translational modification to form an amide that can enhance the biological activity of the polypeptide. In amidation, the C-terminal amino acid (polypeptide-COOH) is modified to form and amide (polypeptide-$CONH_2$). The amide may be formed by post-translational C-terminal amidation. The amino acid to be modified can be followed by a glycine, which provides the amide group. The process of post-translational amidation of a polypeptide derived from a precursor proprotein is well characterized and involves three enzymatic steps (Cuttitta, *The Anatomical Record*, 236:87-93, 1993). Step one involves endoproteolytic cleavage at a pair of basic amino acids near the carboxy terminus of the protein. Step two involves carboxypeptidase-mediated removal of basic residues. Step three is the amidation reaction, which involves oxidation of a terminal glycine to form the amide of the neighboring carboxy terminal amino acid. Glycine is the only known amino acid to function as an amide donor for its neighboring amino acid. Although the free acid and amidated forms of a polypeptide are difficult to distinguish structurally, the amide can be 100-1000 times more biologically active than the free acid form of the polypeptide (Cuttitta, *The Anatomical Record*, 236:87-93, 1993). C-terminal amidation is essential to the biological activity of many polypeptides cDNA (complementary DNA): A piece of DNA lacking internal, non-coding segments (introns) and regulatory sequences that determine transcription. cDNA is synthesized in the laboratory by reverse transcription from messenger RNA extracted from cells.

Collagen: Proteins that are found in the form of elongated fibrils in mammals that are mostly found in fibrous tissues such as tendon, ligament and skin, and is also abundant in cornea, cartilage, bone, blood vessels, the gut, and intervertebral disc. The tropocollagen or "collagen molecule" is a subunit of larger collagen aggregates such as fibrils. It is approximately 300 nm long and 1.5 nm in diameter, made up of three polypeptide strands (called alpha chains), each possessing the conformation of a left-handed helix. In type I collagen, each triple-helix associates into a right-handed super-super-coil that is referred to as the collagen microfibril. Endostain is the first 183 amino acids of collagen.

Conservative variants: "Conservative" amino acid substitutions are those substitutions that do not substantially affect or decrease an activity or of a C-terminal endostain polypeptide, such as the ability of the polypeptide to inhibit fibrosis. Specific, non-limiting examples of a conservative substitution include the following examples:

| Original Residue | Conservative Substitutions |
| --- | --- |
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity, such as the ability of a protein to inhibit fibrosis.

Consists Essentially Of/Consists Of: With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. With regard to a polypeptide, a polypeptide that consists of a specified amino acid sequence does not include any additional amino acid residues, nor does it include additional biological components, such as nucleic acids lipids, sugars, nor does it include labels. A polypeptide that consists or consists essential of a specified amino acid sequence can be glycosylated or have an amide modification. With regard to a polynucleotide, a polynucleotide that consists essentially of a specified nucleic acid sequence if it does not include any additional nucleic acid residues. However, the polypeptide can include additional non-nucleic acid components, such as labels (for example, fluorescent, radioactive, or solid particle labels) or polypeptides. With regard to a polynucleotide, a polynucleotide that consists of a specified nucleic acid sequence does not include any additional nucleic acid residues, nor does it include additional biological components, such as proteins, nor does it include labels.

Degenerate variant: A polynucleotide encoding a C-terminal endostatin polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the C-terminal endostatin polypeptide encoded by the nucleotide sequence is unchanged.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Endostatin: A 183 amino acid proteolytic cleavage fragment corresponding to the C-terminus of collagen XVIII. C-terminal polypeptides of endostatin include consecutive amino acids from the C-terminal region, which is from amino acid 93 to amino acid 183. Exemplary human endostatin polypeptides are set forth in SEQ ID NO: 2 and SEQ ID NO: 13.

Fibrosis: The formation or development of excess fibrous connective tissue in an organ or tissue as a reparative or reactive process, as opposed to a formation of fibrous tissue as a normal constituent of an organ or tissue. Skin and lungs are susceptible to fibrosis. Exemplary fibrotic conditions are scleroderma idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

Heterologous: Originating from separate genetic sources or species. A polypeptide that is heterologous to endostatin originates from a nucleic acid that does not encode endostatin. In specific, non-limiting examples, a polypeptide comprising an C-terminal endostatin polypeptide and a heterologous amino acid sequence includes an Ig (such as $IgG_1$), β-galactosidase, a maltose binding protein, and albumin, hepatitis B surface antigen, or an immunoglobulin amino acid sequence. Generally, an antibody that specifically binds to a protein of interest such as endostatin will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Idiopathic Pulmonary Fibrosis: A condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lung that involves the supporting framework (interstitium) of the lung.

Inhibiting or treating a disease: Inhibiting a disease, such as fibrosis, refers to inhibiting the full development of a disease. In several examples, inhibiting a disease refers to lessening symptoms of a fibrosis, such as the formation of scar tissue or an increase in range of motion or a decrease in pain. "Treatment" refers to a therapeutic intervention that ameliorates a sign or symptom of a disease or pathological condition related to the disease, such as the fibrosis.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Keloid or keloidal scar: A type of scar, which depending on its maturity, is composed of mainly either type III (early) or type I (late) collagen. It is a result of an overgrowth of granulation tissue (collagen type 3) at the site of a healed skin injury which is then slowly replaced by collagen type 1. Keloids are firm, rubbery lesions or shiny, fibrous nodules, and can vary from pink to flesh-colored or red to dark brown in color. A keloid scar is benign, non-contagious, and usually accompanied by severe itchiness, sharp pains, and changes in texture. In severe cases, it can affect movement of skin. Keloids are different than hypertrophic scars, which are raised scars that do not grow beyond the boundaries of the original wound.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the C-terminal endostatin polypeptidesdisclosed herein to provide rotational freedom to the linked polypeptide domains and thereby to promote proper domain folding and presentation to the MHC. By way of example, in a recombinant polypeptide comprising two C-terminal endostatin polypeptides, linker sequences can be provided between them, such as a polypeptide comprising C-terminal endostatin polypeptide-linker-C-terminal endostatin polypeptide. Linker sequences, which are generally between 2 and 25 amino acids in length, are well known in the art and include, but are not limited to, the glycine(4)-serine spacer (×3) described by Chaudhary et al., *Nature* 339:394-397, 1989.

Lysyl oxidase (LOX): Lysyl oxidase is an extracellular copper enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. This results in cross-linking collagen and elastin, which is essential for stabilization of collagen fibrils and for the integrity and elasticity of mature elastin.

Mammal: This term includes both human and non-human mammals. Similarly, the term "subject" includes both human and veterinary subjects.

Matrix metalloproteinase-2: A 72 kDa type IV collagenase also known as gelatinase A. Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. MMP-2 degrades type IV collagen, the major structural component of basement membranes. MMP-2 also degrades additional substrates such as native and denatured collagen I and fibronectin (see the clip.ubc.ca/archive/mmp_timp_folder/mmp_substrates.shtm website).

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a polypeptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes a C-terminal endostatin polypeptide. Generally, operably linked DNA sequences are contiguous and, where necessary to join two protein-coding regions, in the same reading frame.

Peptide Modifications: C-terminal endostatin polypeptides include synthetic embodiments of polypeptides described herein. In addition, analogs (non-peptide organic molecules), derivatives (chemically functionalized polypeptide molecules obtained starting with the disclosed polypeptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the polypeptide side chains may be converted to $C_1$-$C_{16}$ alkoxy or to a $C_1$-$C_{16}$ ester using well-recognized techniques. Phenyl and phenolic rings of the polypeptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the polypeptide backbone and component amino acid side chains, resulting in such peptido- and organomimetics of C-terminal endostatin polypeptide having measurable or enhanced ability to treat fibrosis. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition to achieve a desired effect in a subject being treated. For instance, this can be the amount necessary to induce an immune response, inhibit fibrosis, reduce scar volume or to measurably alter outward symptoms of the fibrotic condition. When administered to a subject, a dosage will generally be used that will achieve target tissue concentrations (for example, in skin cells or lung tissue) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Peptide or Polypeptide: Any chain of amino acids, regardless of length or post-translational modification (e.g., glycosylation or phosphorylation). In one embodiment, the polypeptide is a C-terminal endostatin polypeptide. A polypeptide can be between 5 and 60 amino acids in length. In one embodiment, a polypeptide is from about 10 to about 55 amino acids in length. In yet another embodiment, a polypeptide is from about 20 to about 50 amino acids in length. In yet another embodiment, polypeptide is about 50 amino acids in length. With regard to polypeptides, the word "about" indicates integer amounts. Thus, in one example, a polypeptide "about" 50 amino acids in length is from 49 to 51 amino acids in length.

Post-translational modification: The modification of a newly formed protein; may involve deletion of amino acids, chemical modification of certain amino acids (for example, amidation, acetylation, phosphorylation, glycosylation, formation of pyroglutamate, oxidation/reduction of sulfa group on a methionine, or addition of similar small molecules) to certain amino acids Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Purified: The C-terminal endostatin polypeptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, N.Y., 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Thus, the term purified does not require absolute purity; rather, it is intended as a relative term. For example, a purified nucleic acid is one in which the nucleic acid is more enriched than the nucleic acid in its natural environment within a cell. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Scleroderma: A chronic autoimmune disease characterized by fibrosis (or hardening), vascular alterations, and autoantibodies. There are two major forms, one is a systemic form that includes limited cutaneous scleroderma mainly affects the hands, arms and face, although pulmonary hypertension is frequent. Diffuse cutaneous scleroderma (or systemic sclerosis) is rapidly progressing and affects a large area of the skin and one or more internal organs, frequently the kidneys, esophagus, heart and lungs. Systemic scleroderma in both of its forms can be fatal. The other form of scleroderma is a localized form that has two subtypes: morphea and linear scleroderma. The disclosed endostatin peptides can be used to treat any form of scleroderma.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity.

Sequence identity is frequently measured in terms of percentage identity (or similarity or homology); the higher the percentage, the more similar the two sequences are. Homologs or variants of a C-terminal endostatin polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, J. Mol. Biol. 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a C-terminal endostatin polypeptide are typically characterized by possession of at least 75%, for example at least 80%, sequence identity counted over the full length alignment with the amino acid sequence of endostatin using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Therapeutically effective amount: A quantity of compound, such as the C-terminal endostatin polypeptide sufficient to achieve a desired effect in a subject being treated. For instance, this can be the amount necessary to treat or ameliorate fibrosis, such as skin or lung fibrosis, in a subject. In some embodiments, it is the amount necessary to treat a subject by a measurable amount over a period of time, or to measurably inhibit progression of disease, in a subject. In other embodiments, a therapeutically effective amount is the amount necessary to prophylactically inhibit a disease.

An effective amount of a C-terminal endostatin polypeptide may be administered in a single dose, or in several doses, for example daily, during a course of treatment. However, the effective amount will be dependent on the compound applied, the subject being treated, the severity and type of the affliction, and the manner of administration of the compound.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells and insect cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or peptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

C-Terminal Endostatin Polypeptides

C-terminal endostatin polypeptides and variants thereof are disclosed herein that inhibit fibrosis, such as found in fibrotic conditions, such as but not limited to scleroderma. The polypeptides comprise a C-terminal amino acid sequence of an endostatin protein, but do not include full length endostatin. The endostatin protein can be a mammalian protein, such as from a human, a non-human primate, a canine, a feline, an equine, a bovine, an ovine, a sheep, or a rodent (e.g., mouse or rat). An exemplary nucleotide sequence encoding human endostatin (the amino acid sequence set forth as SEQ ID NO: 2) is:

```
                                            (SEQ ID NO: 1)
ATGCACAGCC ACCGCGACTT CCAGCCGGTG CTCCACCTGG

TTGCGCTCAA CAGCCCCCTG TCAGGCGGCA TGCGGGGCAT
```

```
CCGCGGGGCC GACTTCCAGT GCTTCCAGCA GGCGCGGGCC

GTGGGGCTGG CGGGCACCTT CCGCGCCTTC CTGTCCTCGC

GCCTGCAGGA CCTGTACAGC ATCGTGCGCC GTGCCGACCG

CGCAGCCGTG CCCATCGTCA ACCTCAAGGA CGAGCTGCTG

TTTCCCAGCT GGGAGGCTCT GTTCTCAGGC TCTGAGGGTC

CGCTGAAGCC CGGGGCACGC ATCTTCTCCT TTAACGGCAA

GGACGTCCTG ACCCACCCCA CCTGGCCCCA GAAGAGCGTG

TGGCATGGCT CGGACCCCAA CGGGCGCAGG CTGACCGAGA

GCTACTGTGA GACGTGGCGG ACGGAGGCTC CCTCGGCCAC

GGGCCAGGCC TACTCGCTGC TGGGGGGCAG GCTCCTGGGG

CAGAGTGCCG CGAGCTGCCA TCACGCCTAC ATCGTGCTAT

GCATTGAGAA CAGCTTCATG ACTGCCTCCA AGTAG
```

See also GENBANK® Accession Nos. NM030582.3; NM130444.2; NM130445.2, all of which are incorporated herein by reference.

Another exemplary nucleotide sequence encoding a human endostatin (the amino acid sequence set forth as SEQ ID NO: 13) is:

```
                                      (SEQ ID NO: 12)
CACAGCCACCGC GACTTCCAGC CGGTGCTCCACCTGGTTGCG

CTCAACAGCC CCCTGTCAGG CGGCATGCGG GGCATCCGCG

GGGCCGACTT CCAGTGCTTC CAGCAGGCGC GGGCCGTGGG

GCTGGCGGGC ACCTTCCGCG CCTTCCTGTCCTCGCGCCTG

CAGGACCTGT ACAGCATCGT GCGCCGTGCC GACCGCGCAG

CCGTGCCCATCGTCAACCTC AAGGACGAGC TGCTGTTTCC

CAGCTGGGAG GCTCTGTTCT CAGGCTCTGAGGGTCCGCTG

AAGCCCGGGG CACGCATCTT CTCCTTTGAC GGCAAGGACG

TCCTGAGGCA CCCCACCTGG CCCCAGAAGA GCGTGTGGCA

TGGCTCGGAC CCCAACGGGC GCAGGCTGAC CGAGAGCTAC

TGTGAGACGT GGCGGACGGA GGCTCCCTCG GCCACGGGCC

AGGCCTCCTC GCTGCTGGGG GGCAGGCTCC TGGGGCAGAG

TGCCGCGAGC TGCCATCACG CCTACATCGTGCTCTGCATT

GAGAACAGCT TCATGACTGC CTCCAAGTAG
```

An exemplary human endostatin protein is:

```
                                      (SEQ ID NO: 2)
HSHRDFQPVL HLVALNSPLS GGMRGIRGAD FQCFQQARAV

GLAGTFRAFL SSRLQDLYSI VRRADRAAVP IVNLKDELLF

PSWEALFSGS EGPLKPGARI FSFNGKDVLT HPTWPQKSVW

HGSDPNGRRL TESYCETWRT EAPSATGQAY SLLGGRLLGQ

SAASCHHAYI VLCIENSFMTASK
```

This protein is 183 amino acids in length, and is identical to GENBANK® Accession number AAF01310 except that it is lacking the initiator methionine of AAF01310).

Another exemplary endostatin protein is:

```
                                      (SEQ ID NO: 13)
HSHRDFQPVL HLVALNSPLS GGMRGIRGAD FQCFQQARAV

GLAGTFRAFL SSRLQDLYSI VRRADRAAVP IVNLKDELLF

PSWEALFSGS EGPLKPGARI FSFDGKDVLR HPTWPQKSVW

HGSDPNGRRL TESYCETWRT EAPSATGQAS SLLGGRLLGQ

SAASCHHAYI VLCIENSFMTASK
```

See also GENBANK® Accession No. CAB90482, which is incorporated herein by reference.

SEQ ID NO: 2 is identical to SEQ ID NO: 13, with the exception of three amino acid substitutions, indicated by underlining.

An exemplary nucleotide sequence encoding mouse endostatin is:

```
                                      (SEQ ID NO: 3)
CATACTCATC AGGACTTTCA GCCAGTGCTC CACCTGGTGG

CACTGAACAC CCCCCTGTCT GGAGGCATGC GTGGTATCCG

TGGAGCAGAT TTCCAGTGCT TCCAGCAAGC CCGAGCCGTG

GGGCTGTCGG GCACCTTCCG GGCTTTCCTG TCCTCTAGGC

TGCAGGATCT CTATAGCATC GTGCGCCGTG CTGACCGGGG

GTCTGTGCCC ATCGTCAACC TGAAGGACGA GGTGCTATCT

CCCAGCTGGG ACTCCCTGTT TTCTGGCTCC CAGGGTCAAC

TGCAACCCGG GGCCCGCATC TTTTCTTTTG ACGGCAGAGA

TGTCCTGAGA CACCCAGCCT GGCCGCAGAA GAGCGTATGG

CACGGCTCGG ACCCCAGTGG GCGGAGGCTG ATGGAGAGTT

ACTGTGAGAC ATGGCGAACT GAAACTACTG GGGCTACAGG

TCAGGCCTCC TCCCTGCTGT CAGGCAGGCT CCTGGAACAG

AAAGCTGCGA GCTGCCACAA CAGCTACATC GTCCTGTGCA

TTGAGAATAG CTTCATGACC TCTTTCTCCA AA.
```

An exemplary mouse endostatin protein is:

```
                                      (SEQ ID NO: 4)
HTHQDFQPVL HLVALNTPLS GGMRGIRGAD FQCFQQARAV

GLSGTFRAFL SSRLQDLYSI VRRADRGSVP IVNLKDEVLS

PSWDSLFSGS QGQLQPGARI FSFDGRDVLR HPAWPQKSVW

HGSDPSGRRL MESYCETWRT ETTGATGQAS SLLSGRLLEQ

KAASCHNSYI VLCIENSFMT SFSK
```

This protein is identical to GENBANK® Accession number AAF69009. The nucleotide and amino acid sequences of other species are also publicly available.

In one embodiment, the C-terminal endostatin polypeptide comprises about 10 to about 60 consecutive amino acids of the C-terminal region of an endostatin protein, but does not include a full length endostatin protein, or the N-terminal region of an endostatin protein. The peptide can include from about 10 to about 55 consecutive amino acids or from about 20 to about 54 consecutive amino acids of the C-terminal region of an endostatin protein, such as about 53 consecutive amino acids of the C-terminal region of an endostatin protein (such as SEQ ID NO: 2). For example, the peptide may include about 40, about 45, about, 46, about 47, about 48, about 49, about 50, about 51, about 52 or about 53 consecutive amino acids of the C-terminal region on an endostatin protein, such as amino acids 93 to 183 of endostatin, for example SEQ ID NO: 2, SEQ ID NO: 13 or SEQ ID NO: 4. In the context of an amino acid or nucleic acid sequence, "about" means within one residue (one more or one less than the specified number).

The endostatin peptide can include 40, 45, 46, 47, 48, 49 50, 51, 52, 53 consecutive amino acids of the C-terminal region of an endostatin protein. In some examples the peptide consists of 40, 45, 46, 47, 48, 49, 50, 51, 52, 53 consecutive amino acids of the C-terminal region of an endostatin protein, such as but not limited to SEQ ID NO: 2, SEQ ID NO: 4 or SEQ ID NO: 13. In some embodiments, the peptide includes or consists of at least 30 amino acids of amino acids 133 to 180 of endostatin, or a variant thereof that has anti-fibrotic activity.

The endostatin peptide may include, consist of or consist essentially of about amino acid 120, 125, 130, 131, 132, 133, 134 or 135 to about amino acids 175, 180, 181, 182 or 183 of an endostatin protein, such as SEQ ID NO: 2, SEQ ID NO: 4 or SEQ ID NO: 13. In several examples, the peptide includes, consists of or consists essentially of amino acid 120 to 183, 125 to 183, 130 to 183, 131 to 183, 132 to 183, 134 to 183, 135 to 183, 120 to 180, 125 to 180, 130 to 180, 131 to 180, 132 to 180, 133 to 180, 134 to 180 or 135 to 180 of SEQ ID NO: 2, SEQ ID NO: 4 or SEQ ID NO: 13. In specific examples, the peptide includes, consists of, or consists essentially of amino acids 133-180 of SEQ ID NO: 2, amino acids 133-180 of SEQ ID NO: 4 or amino acids 133-180 of SEQ ID NO: 13. In this context, "consists essentially of" means that a peptide does not include additional amino acid residues but can include additional components, such as a label.

Other endostatin peptide variants disclosed herein may comprise, consist of or consist essentially of an amino acid sequence that has at least about 70%, 80%, 90%, 95%, 98% or 99% identity or homology with a C-terminal endostatin polypeptide. C-terminal endostatin polypeptides do not include a full length endostatin protein or the N-terminal region of an endostatin protein (such as amino acids 1-92 of SEQ ID NO: 2).

In some non-limiting examples, C-terminal endostatin polypeptides can include substitutions, such as conservative amino acid substitutions, in a naturally occurring C-terminal endostatin polypeptide (see SEQ ID NO: 2, 4 or 13) in at most about 1, 2, 3, 4, 5 substitutions would be expected to retain anti-fibrotic activity. The C-terminal endostatin polypeptide can include at most 1, at most 2, at most 3 or at most 4 amino acid substitutions, such as conservative amino acid substitutions.

Peptides that are similar to the sequences described above may contain substitutions, deletions or additions. The differences are preferably in regions that are not significantly conserved among different species. Such regions can be identified by aligning the amino acid sequences of endostatin proteins from various animal species. Thus, the endostatin peptide can include, consist essentially of, or consist of at least 40, at least 45, at least 46, at least 47, at least 48, at least 50, at least 51, at least 52 or all of the amino acids set forth as amino acids 133-180 of SEQ ID NO: 2, SEQ ID NO: 4 or SEQ ID NO: 13. Alternatively, the endostatin peptide can include at most 1, 2, 3, 4 or 5 amino acid substitutions in one of these sequences, provided the peptide has anti-fibrotic activity. The peptide can be 40, 45, 46, 47, 48, 49, 50, 51, 52 or 53 amino acids in length. The peptide does not include the entire sequence of endostatin, or the N-terminal region, such as of SEQ ID NO: 2, SEQ ID NO: 4 or SEQ ID NO: 13. In additional embodiments, the peptide is at most 40, 45, 46, 47, 48, 49, 50, 51, 52 or 53 amino acids in length, such as peptide that is 40, 45, 46, 47, 48, 49, 50, 51, 52 or 53 amino acids in length. In some embodiments, the peptide is modified, such as to include a C-terminal amide. Any of the C-terminal endostatin polypeptides disclosed herein can include a C-terminal amide.

The following is an alignment of the human (amino acid 133-180 of endostatin), mouse, rat, cow collagen XVIII amino acid sequences, and human collagen XV:

| | |
|---|---|
| Human | SYCETWRTEAPSATGQASSLLGGRLLGQSAASCHHAYIVLCIENSFMT |
| | <u>SYCETWRTE</u>  ATGQASSLL GRLL Q <u>AASCH</u> ++<u>YIVLCIENSFMT</u> |
| Mouse | SYCETWRTETTGATGQASSLLSGRLLEQKAASCHNSYIVLCIENSFMT |
| Rat | SYCETWRTEATGVTGQASSLLSGRLLEQKAESCHNSYIVLCIENSFMT |
| Cow. . . | SYCETWRTDSRAATGQASSLLAGRLLEQKAAGCHNAFIVLCIENSFMT |
| HumXV | N<u>Y</u>CEAWRTADIAVTGLASPLSTGKILDQKAYSCANRL<u>IVLCIENSFMT</u> |

(amino acids 133-141, amino acids 145-153, amino acids 155-158, 162-166, amino acids 169-180 for the human sequence above, see SEQ ID NO: 2, for the mouse sequence above, see SEQ ID NO: 4, for the rat sequence above, see SEQ ID NO: 9, for the cow sequence above, see SEQ ID NO: 10; human collagen XV is SEQ ID NO: 11)

In some embodiments, the double underlined amino acids above show those regions of SEQ ID NO: 2, 4 or 13 should be conserved to preserve anti-fibrotic activity of the polypeptide. In further embodiments, the underlined amino acids should be retained in order to preserve anti-fibrotic activity of the polypeptide. Thus, in some embodiments, the C-terminal endostatin polypeptide comprises amino acids 133-141, 145-153, 155-158, 162-166 and 169-180 of SEQ ID NO: 2, SEQ ID NO: 4 or SEQ ID NO: 13. In one example, the A at position 145 is conserved.

E4 is amino acids 133-180 of human endostatin (see amino acids 133-180 of SEQ ID NO: 2) and includes a C-terminal amide. In additional embodiments, a region that should be retained in the peptide to retain anti-fibrotic activity is one or both potential phosphorylation sites in the first seven amino acids of E4 that are conserved: SYCE and TWR (amino acids 1-4 and 5-7 of E4, respectively, see also amino acids 133-136 and 137-139 of SEQ ID NO: 2 or SEQ ID NO: 13). In several embodiments, regions that can be retained in the peptide to retain anti-fibrotic activity are one or both potential myristilation sites: GQaySL and GQsaAS (amino acids 15-20 and 27-32 of E4, respectively, see amino acids 147-152 and amino acids 159-164 of SEQ ID NO: 2 or SEQ ID NO: 13). Thus, in some embodiments, the C-terminal endostatin polypeptide includes zero, or at most 1, at most 2, at most 3, at most 4, or at most 5 substitutions in amino acids 133-180 of SEQ ID NO: 2, SEQ ID NO: 4 or SEQ ID NO: 13, wherein the substitutions are not in amino acids 133-141, 145-153, 155-158, 162-166 and 169-180 of SEQ ID NO: 2, SEQ ID NO: 4 or SEQ ID NO: 13, and includes a C-terminal amide.

In other embodiments, amino acids can be substituted that differ between the human and mouse sequences without affecting anti-fibrotic activity. In other embodiments, the bolded and italicized amino acids shown above in the human sequence are those amino acids that can be substituted while preserving anti-fibrotic activity. For example, amino acids 142-144, 154, 159-161, and 181-183 of the amino acid sequence can be altered in the C-terminal endostatin polypeptide. These amino acids can be substituted, for example, with those found in another species, as shown above (SEQ ID NOs: 9-10). For example, the C-terminal endostatin polypeptide can include amino acids 133-180 of SEQ ID NO: 2 or SEQ ID NO: 13, wherein amino acids 142-144, 154, and amino acids 159-161 are substituted. This polypeptide can include a C-terminal amide.

Other amino acids that can be substituted, inserted or deleted at these or other locations can be identified by mutagenesis studies coupled with biological assays. The above alignment is provided only as a guideline.

Also encompassed herein are C-terminal endostatin polypeptides that are fused to a heterologous peptide, such as a peptide that can be used for detecting; purifying; stabilizing; or solubilizing the endostatin polypeptide. These polypeptides do not include a full length endostatin protein or an N-terminal region of an endostatin protein. In one example, a C-terminal polypeptide can be linked to an immunoglobulin (Ig) constant heavy or light chain domain or portion thereof at its N-terminus. For example, a polypeptide, such as but not limited to amino acids 133-180 of SEQ ID NO: 2, SEQ ID NO: 4 or SEQ ID NO: 13(e.g., E4) may be linked to a CH1, CH2 and/or CH3 domain of a heavy chain. If the constant region is from a light chain, it can be from a kappa or lambda light chain. If the constant region is from a heavy chain, it can be from an antibody of any one of the following classes of antibodies: IgG, IgA, IgE, IgD, and IgM. IgG can be an IgG$_1$, IgG$_2$, IgG$_3$ or IgG$_4$. The constant domain may be an Fc fragment. The constant domain can be from a mammalian antibody, such as a human antibody. Soluble receptor-IgG fusion proteins are common immunological reagents and methods for their construction are known in the art (see, for example, U.S. Pat. Nos. 5,225,538, 5,726,044; 5,707,632; 750,375, 5,925,351, 6,406,697 and Bergers et al. Science 1999 284: 808-12). In one example, the immunoglobulin is the constant part of the heavy chain of human IgG, particularly IgG$_1$, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

An Fc portion of human IgG$_1$ which includes the hinge region, and domains CH2 and CH3 has the nucleotide sequence:

(SEQ ID NO: 5)
```
GAG CCC AAA TCT TGT GAC AAA ACT CAC ACA TGC CCA
CCG TGC CCA GCA CCT GAA CTC CTG GGG GGA CCG TCA
GTC TTC CTC TTC CCC CCA AAA CCC AAG GAC ACC CTC
ATG ATC TCC CGG ACC CCT GAG GTC ACA TGC GTG GTG
GTG GAC GTG AGC CAC GAA GAC CCT GAG GTC AAG TTC
AAC TGG TAC GTG GAC GGC GTG GAG GTG CAT AAT GCC
AAG ACA AAG CCG CGG GAG GAG CAG TAC AAC AGC ACG
TAC CGT GTG GTC AGC GTC CTC ACC GTC CTG CAC CAG
GAC TGG CTG AAT GGC AAG GAG TAC AAG TGC AAG GTC
TCC AAC AAA GCC CTC CCA GCC CCC ATC GAG AAA ACC
ATC TCC AAA GCC AAA GGG CAG CCC CGA GAA CCA CAG
GTG TAC ACC CTG CCC CCA TCC CGG GAT GAG CTG ACC
AAG AAC CAG GTC AGC CTG ACC TGC CTG GTC AAA GGC
TTC TAT CCC AGC GAC ATC GCC GTG GAG TGG GAG AGC
AAT GGG CAG CCG GAG AAC AAC TAC AAG ACC ACG CCT
CCC GTG CTG GAC TCC GAC GGC TCC TTC TTC CTC TAC
AGC AAG CTC ACC GTG GAC AAG AGC AGG TGG CAG CAG
GGG AAC GTC TTC TCA TGC TCC GTG ATG CAT GAG GCT
CTG CAC AAC CAC TAC ACG CAG AAG AGC CTC TCC CTG
TCT CCG GGT AAA TGA,
``` which encodes a polypeptide having the amino acid sequence:

(SEQ ID NO: 6)
```
Glu Pro Lys Ser Cys Asp Lys Thr His Thr Cys Pro
Pro Cys Pro Ala Pro Glu Leu Leu Gly Gly Pro Ser
Val Phe Leu Phe Pro Pro Lys Pro Lys Asp Thr Leu
Met Ile Ser Arg Thr Pro Glu Val Thr Cys Val Val
Val Asp Val Ser His Glu Asp Pro Glu Val Lys Phe
Asn Trp Tyr Val Asp Gly Val Glu Val His Asn Ala
Lys Thr Lys Pro Arg Glu Glu Gln Tyr Asn Ser Thr
Tyr Arg Val Val Ser Val Leu Thr Val Leu His Gln
Asp Trp Leu Asn Gly Lys Glu Tyr Lys Cys Lys Val
Ser Asn Lys Ala Leu Pro Ala Pro Ile Glu Lys Thr
Ile Ser Lys Ala Lys Gly Gln Pro Arg Glu Pro Gln
Val Tyr Thr Leu Pro Pro Ser Arg Asp Glu Leu Thr
Lys Asn Gln Val Ser Leu Thr Cys Leu Val Lys Gly
Phe Tyr Pro Ser Asp Ile Ala Val Glu Trp Glu Ser
Asn Gly Gln Pro Glu Asn Asn Tyr Lys Thr Thr Pro
Pro Val Leu Asp Ser Asp Gly Ser Phe Phe Leu Tyr
Ser Lys Leu Thr Val Asp Lys Ser Arg Trp Gln Gln
Gly Asn Val Phe Ser Cys Ser Val Met His Glu Ala
Leu His Asn His Tyr Thr Gln Lys Ser Leu Ser Leu
Ser Pro Gly Lys.
```

Constant Ig domains can also contain one or more mutations that reduce or eliminate one or more effector function, e.g., binding to Fc receptors and complement activation (see, for example, Morrison, Annu. Rev. Immunol., 10, pp. 239-65 (1992); Duncan and Winter (1988) Nature 332: 738-740; and Xu et al. (1994) J Biol. Chem. 269: 3469-3474). For example, mutations of amino acids corresponding to Leu 235 and Pro 331 of human IgG$_1$ to Glu and Ser respectively, are provided. Such constructs are further described in U.S. Pat. No. 6,656,728.

The C-terminal endostatin polypeptide can also be linked to a linker sequence with a thrombin cleavage site, such as between the C-terminal endostatin polypeptide and a heterologous polypeptide. An exemplary nucleotide sequence encoding such a site has the following nucleotide sequence: 5' TCT AGA GGT GGT CTA GTG CCG CGC GGC AGC GGT TCC CCC GGG TTG CAG 3' (SEQ ID NO: 7), which encodes a polypeptide having the amino acid sequence: Ser Arg Gly Gly Leu Val Pro Arg Gly Ser Gly Ser Pro Gly Leu Gln (SEQ ID NO: 8). A C-terminal endostatin polypeptide can also be fused to a signal sequence. For example, when prepared recombinantly, a nucleic acid encoding the peptide can be linked at its 5' end to a signal sequence, such that the peptide is secreted from the cell.

Peptides can be used as a substantially pure preparation, such as wherein at least about 90% of the peptides in the preparation are the desired peptide. Compositions comprising at least about 50%, 60%, 70%, or 80% of the desired peptide may also be used. Peptides can be denatured or non-denatured and may be aggregated or non-aggregated as a result thereof.

Other C-terminal endostatin polypeptides that are encompassed herein are those that include modified amino acids. Exemplary peptides are derivative peptides that may be one modified by glycosylation, pegylation, phosphorylation or any similar process that retains at least one biological function of the peptide from which it was derived. Peptides may also comprise one or more non-naturally occurring amino acids. For example, nonclassical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary). In other specific embodiments, branched versions of the peptides listed herein are provided, such as by substituting one or more amino acids within the sequence with an amino acid or amino acid analog with a free side chain capable of forming a peptide bond with one or more amino acids (and thus capable of forming a "branch"). Cyclical peptides are also contemplated.

Also included are peptide derivatives which are differentially modified during or after synthesis, such as by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

In one example, the peptide includes a carboxy terminal amide. One specific non-limiting example of this type of C-terminal endostatin polypeptide is E4 (see, for example, amino acids 133-180 of SEQ ID NO: 13), which is described in detail in the examples section below. This peptide, or any of the C-terminal endostatin polypeptides disclosed herein can be amidated at the C-terminus.

Also provided are derivatives of C-terminal endostatin polypeptides, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into non-peptide compounds with the activity of the parent peptides.

Mimetopes of the C-terminal endostatin polypeptides are included in the present disclosure. Such peptidomimetics can have such attributes as being non-hydrolyzable (e.g., increased stability against proteases or other physiological conditions which degrade the corresponding peptide), increased specificity and/or potency for stimulating cell differentiation. For illustrative purposes, peptide analogs can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1: 1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988).

In addition to a variety of side-chain replacements which can be carried out to generate peptidomimetics, the present disclosure specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides. Additionally, peptidomimietics based on more substantial modifications of the backbone of a peptide can be used. Peptidomimetics which fall in this category include (i) retro-inverso analogs, and (ii) N-alkyl glycine analogs (so-called peptoids). Furthermore, the methods of combinatorial chemistry can be used to produce peptidomimetics. For example, one embodiment of a so-called "peptide morphing" strategy focuses on the random generation of a library of peptide analogs that comprise a wide range of peptide bond substitutes. In an exemplary embodiment, the peptidomimetic can be derived as a retro-inverso analog of the peptide. Such retro-inverso analogs can be made according to the methods known in the art, such as that described by the Sisto et al. U.S. Pat. No. 4,522,752. A retro-inverso analog can be generated as described, for example in PCT Publication No. WO 00/01720. A mixed peptide, such as one including some normal peptide linkages, can be generated. As a general guide, sites which are most susceptible to proteolysis are typically altered, with less susceptible amide linkages being optional for mimetic switching. The final product, or intermediates thereof, can be purified by HPLC.

In some embodiments, peptides can include at least one amino acid or every amino acid that is a D stereoisomer. Other peptides can include at least one amino acid that is reversed. The amino acid that is reversed may be a D stereoisomer. Every amino acid of a peptide may be reversed and/or every amino acid can be a D stereoisomer. In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, for example in PCT Publication No. WO 00/01720. The final product can be purified by HPLC to yield the pure retro-enantio analog. In still another illustrative embodiment, trans-olefin derivatives can be made for the subject peptide. Trans-olefin analogs can be synthesized according to the method of Y. K. Shue et al. (1987) Tetrahedron Letters 28:3225 and as described in PCT Publication WO 00/01720. It is further possible to couple pseudodipeptides synthesized by the above method to other pseudodipeptides, to make peptide analogs with several olefinic functionalities in place of amide functionalities. Still another class of peptidomimetic derivatives include the phosphonate derivatives. The synthesis of such phosphonate derivatives can be adapted from known synthesis schemes (see, for example, Loots et al. in Peptides: Chemistry and Biology, (Escom Science Publishers, Leiden, 1988, p. 118)); Petrillo et al. in Peptides: Structure and Function (Proceedings of the 9th American Peptide Symposium, Pierce Chemical Co. Rockland, Ill., 1985).

Many other peptidomimetic structures are known in the art and can be readily adapted for use in the subject peptidomimetics. For example, a peptidomimetic may incorporate the 1-azabicyclo[4.3.0]nonane surrogate (see Kim et al. (1997) J. Org. Chem. 62:2847), or an N-acyl piperazic acid (see Xi et al. (1998) J. Am. Chem. Soc. 120:80), or a 2-substituted piperazine moiety as a constrained amino acid analogue (see Williams et al. (1996) J. Med. Chem. 39:1345-1348). In still other embodiments, certain amino acid residues can be replaced with aryl and bi-aryl moieties, such as monocyclic or bicyclic aromatic or heteroaromatic nucleus, or a biaromatic, aromatic-heteroaromatic, or biheteroaromatic nucleus. The subject peptidomimetics can be optimized such as by combinatorial synthesis techniques combined with high throughput screening. Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting fibrosis. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (for example, plants, animals, bacteria and fungi).

All of the C-terminal endostatin polypeptides of use in the disclosed methods have anti-fibrotic activity. For example, they can reduce or inhibit fibrosis by a factor of at least about 50%, 60%, 70% 80%, 90%, or 2 fold, 5 fold, 10 fold, 30 fold or 100 fold, as compared to a control, such as in an assay described herein.

The C-terminal endostatin polypeptides (including amidated forms of the peptides) can be readily synthesized by automated solid phase procedures well known in the art. Techniques and procedures for solid phase synthesis are described in *Solid Phase Peptide Synthesis: A Practical Approach*, by E. Atherton and R. C. Sheppard, published by IRL, Oxford University Press, 1989. Alternatively, these peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., Int. J. Peptide Protein Res. 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing peptides of the present disclosure are described in Nakagawa et al., *J. Am. Chem. Soc.* 107:7087-7092, 1985. Peptides of the disclosure can also be readily purchased from commercial suppliers of synthetic peptides. Such suppliers include, for example, Advanced ChemTech (Louisville, Ky.), Applied Biosystems (Foster City, Calif.), Anaspec (San Jose, Calif.), and Cell Essentials (Boston, Mass.).

Polynucleotides Encoding the C-Terminal Endostatin Polypeptides and Host Cells

Polynucleotides encoding the C-terminal endostatin polypeptides disclosed herein are also provided. These polynucleotides include DNA, cDNA and RNA sequences which encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W. H. 5 Freeman and Co., N.Y.).

A nucleic acid encoding a C-terminal endostatin polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N.Y., 1989). Polynucleotides also can be isolated by screening genomic or cDNA libraries with probes selected from the sequences of the desired polynucleotide under stringent hybridization conditions.

The polynucleotides encoding a C-terminal endostatin polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2µ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. The polynucleotides can also be designed to express in insect cells.

The C-terminal endostatin polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the C-terminal endostatin polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a C-terminal endostatin polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a C-terminal endostatin polypeptide. The recombinant virus containing such a chimeric gene is effective at expressing the C-terminal endostatin polypeptide. In one example, the vaccine viral vector comprises (A) a segment comprised of (i) a first DNA sequence encoding a C-terminal endostatin polypeptide and (ii) a poxvirus promoter, wherein the poxvirus promoter is adjacent to and exerts transcriptional control over the DNA sequence encoding a C-terminal endostatin polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxviral vectors that encode a C-terminal endostatin polypeptide include at least one expression control element operationally linked to the nucleic acid sequence encoding the C-terminal endostatin polypeptide. The expression control elements are inserted in the poxviral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the C-terminal endostatin polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the C-terminal endostatin polypeptide, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419). In particular, recombinant viral vectors such as a poxyiral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

DNA sequences encoding a C-terminal endostatin polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a C-terminal endostatin polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, Neurospora, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a C-terminal endostatin polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Therapeutic Methods and Pharmaceutical Compositions

The C-terminal endostatin polypeptides disclosed herein, or nucleic acids encoding the C-terminal endostatin polypeptides, can be used to treat fibrosis. In several examples, the C-terminal endostatin polypeptides, or nucleic acid encoding these polypeptides are of use to decrease fibrosis, such as in a subject. Thus, in several embodiments, the methods include administering to a subject a therapeutically effective amount of one or more of the C-terminal endostatin polypeptides disclosed herein, or polynucleotides encoding these polypeptides, in order to decrease fibrosis. In some examples, the C-terminal endostatin polypeptide comprises or consists of amino acids 133-180 of SEQ ID NO: 2, SEQ ID NO: 4 or SEQ ID NO: 13. However, any of the C-terminal endostatin polypeptides disclosed herein can be used to decrease fibrosis. In some embodiments, the peptides can be administered as a unit dose.

Suitable subjects include those with a fibrosis of the skin or lungs, but fibrosis of any tissue can be treated using the methods disclosed herein. In one example, the subject has scleroderma. In other examples, the subject has idiopathic pulmonary fibrosis, morphea, fibrosis as a result of Graft-Versus-Host Disease (GVHD), a keloid or hypertrophic scar, subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

In further examples, the methods are used to treat the systemic form of scleroderma, such as limited cutaneous scleroderma- or diffuse cutaneous scleroderma (or systemic sclerosis). The methods can be used to treat the localized form of scleroderma, including morphea and linear scleroderma.

The methods can include selecting a subject in need of treatment, such as a subject with a fibrotic disease, such as scleroderma, idiopathic pulmonary fibrosis, morphea, a keloid scar, a hypertrophic scar, or subepithelial fibrosis. In exemplary applications, compositions are administered to a subject having a fibrotic disease, such as scleroderma, idiopathic pulmonary fibrosis, morphea, a keloid scar, a hypertrophic scar, or subepithelial fibrosis, or any of the disorders listed above, in an amount sufficient to reduce the fibrosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A method is provided herein for decreasing skin thickness. The method includes administering a therapeutically effective amount of a C-terminal endostatin polypeptide, thereby decreasing skin thickness. In another embodiment, and methods is provided for decreasing lung fibrosis. The method includes administering a therapeutically effective amount of a C-terminal endostatin polypeptide, thereby decreasing skin thickness. Any of the C-terminal endostatin polypeptides disclosed herein can be used in these methods. In some embodiments, the C-terminal endostatin polypeptide comprises, or consists of, amino acids 133-180 of SEQ ID NO: 2, SEQ ID NO: 4 or SEQ ID NO: 13.

Methods are provided herein for decreasing lysyl oxidase (LOX), such as transforming growth factor (TGF)-β induced LOX. The method includes contacting a cell with an effective amount of a C-terminal endostatin polypeptide, thereby decreasing LOX. The methods can be practiced in vivo or in vitro. In some embodiments, the methods include comparing the amount of LOX produced by a cell contacted with a C-terminal endostatin polypeptide to a control. The control can be a standard value, or the amount of LOX produced by a cell not contacted with the C-terminal endostatin polypeptide, such as a cell contacted with a carrier.

Methods are provided herein for increasing matrix metalloproteinase-2 (MMP-2). The method includes contacting a cell with an effective amount of a C-terminal endostatin polypeptide, thereby increasing MMP-2 production. The methods can be practiced in vivo or in vitro. In some embodiments, the methods include comparing the amount of MMP-2 produced by a cell contacted with a C-terminal endostatin polypeptide to a control The control can be a standard value, or the amount of MMP-2 produced by a cell not contacted with the C-terminal endostatin polypeptide, such as a cell contacted with a carrier.

A C-terminal endostatin polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intradermal, intrathecal, intramuscular, subcutaneous, intraperitoneal or intravenous injection, but even oral, nasal, transdermal or anal administration is contemplated. In one embodiment, administration is by subcutaneous, intradermal, or intramuscular injection. In another embodiment, administration is by intraperitoneal or intrathecal administration. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra).

For treatment of the skin, a therapeutically effective amount of at least one C-terminal endostatin polypeptide, or a nucleic acid encoding the peptide, can be locally administered to the affected area of the skin, such as in the form of an ointment. In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one C-terminal endostatin polypeptide, or polynucleotide encoding the peptide can be administered in a composition that contains a synthetic or natural hydrophilic polymer as the carrier. Examples of such polymers include hydroxypropyl cellulose and polyethylene glycol. One or more C-terminal endostatin polypeptides, or polynucleotide encoding the polypeptides, can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more C-terminal endostatin polypeptide, or polynucleotide encoding the peptide can also be incorporated into bandages and dressings.

For administration by inhalation, the C-terminal endostatin polypeptide, or polynucleotide encoding the peptide can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, the C-terminal endostatin polpeptide, such as, but not limited to E4, can be administered by inhalation. For example, the C-terminal endostatin polypeptide can be administered in an aerosolized form, such as using a nebulizer or a metered dose inhaler. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMIST®), and ultrasonic nebulizers (such as the DeVilbiss ULTRA-NEB®).

The endostatin polypeptide can be dissolved in a carrier, such as saline, and atomized using the devices above. The associated aerosols can be collected using a NEXT GENERATION IMPACTOR® (NGI) (MSP Corp., Shoreview, Minn.), which uses a series of aerodynamic stages to separate and collect the aerosol into separate fractions based on droplet size. Since droplet size is the primary determinant of deposition location in the lungs, this device allows us to specifically isolate the portion of the liquid aerosol that will deposit in the small airways and alveoli.

Aerosol particle size is often expressed in terms of mass median aerodynamic diameter (MMAD), a parameter that is based on particle size, shape, and density. For a spherical particle, MMAD is equal to MMD $(p^{1/2})$, in which MMD is mass median diameter and r is the bulk density. For a non-spherical particle, MMAD is equal to MMD $(p/x)^{1/2}$, in which X is the shape factor. Thus, particles with larger than unit density will have actual diameters smaller than their MMAD.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

A therapeutically effect amount of a C-terminal endostatin polypeptide, or polynucleotide encoding the peptide can be administered in the pharmaceutically acceptable carrier. Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one C-terminal endostatin polypeptide, or polynucleotide encoding the peptide, either in vivo or ex vivo, to decrease fibrosis. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the active ingredient can be combined with carriers suitable for incorporation into tablets, pills, capsules, liquids, gels, syrups, slurries, suspensions and the like. The active ingredient can be formulated for parenteral administration by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the at least one C-terminal endostatin polypeptide, or polynucleotide encoding the peptide can be contained within or conjugated with a heterologous protein, hydrocarbon or lipid, whether for in vitro or in vivo administration. Co-administration can be such that the at least one C-terminal endostatin polypeptide, or polynucleotide encoding the peptide is administered before, at substantially the same time as, or after the protein, hydrocarbon, or lipid. In one embodiment, the at least one C-terminal endostatin polypeptide, or polynucleotide encoding the peptide is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the at least one C-terminal endostatin polypeptide, or polynucleotide encoding the peptide is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as scleroderma. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with oligodeoxynucleotides (see U.S. Pat. No. 6,218,371). For use in vivo, nucleic acids and peptides are preferably relatively resistant to degradation (such as via endo- and exo-nucleases). Thus, modifications, such as the inclusion of a C-terminal amide, can be used.

The therapeutically effective amount of C-terminal endostatin polypeptide, or polynucleotide encoding the peptide will be dependent on the C-terminal endostatin polypeptide, or polynucleotide encoding the peptide, that is utilized, the subject being treated, the severity and type of the affliction, and the manner of administration. For example, a therapeutically effective amount of a polynucleotide encoding the peptide can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound the age, weight, sex and physiological condition of the subject.

With regard to the administration of nucleic acids, one approach to administration of nucleic acids is direct treatment with plasmid DNA, such as with a mammalian expression plasmid. As described above, the nucleotide sequence encoding a N-terminal endostatin peptide can be placed under the control of a promoter to increase expression of the molecule.

When a viral vector is utilized for administration in vivo, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more C-terminal endostatin polypeptides to be administered is based on the titer of virus particles. An exemplary range of the immunogen to be administered is $10^5$ to $10^{10}$ virus particles per mammal, such as a human.

In one specific, non-limiting example, a pharmaceutical composition for intravenous administration would include about 0.1 µg to 10 mg of C-terminal endostatin polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remingtons Pharmaceutical Sciences, 19th Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a further method, an additional agent is administered. In one example, this administration is sequential. In other examples, the additional agent is administered simultaneously with the C-terminal endostatin polypeptide.

For the treatment of scleroderma, examples of additional agents that can be used with a C-terminal endostatin polypeptides include nifedipine, amlodipine, diltiazem, felodipine, or nicardipine. An investigational drug Gleevec, is also used for the treatment of scleroderma. Gleevec or other tyrosine kinase inhibitors can be used with the C-terminal endostatin polypeptides disclosed herein. Patients with lung involvement of scleroderma benefit from oxygen therapy; the C-terminal endostatin polypeptides disclosed herein can be administered with this therapy.

For the treatment of fibrosis of the skin and scleroderma, additional agents of use are d-penicillamine, colchicine, Relaxin, steroids, and cyclosporine. C-terminal endostatin polypeptides also can be used in combination with immunosuppressive agents. Additionally, the C-terminal endostatin polypeptides can be used with methotrexate, cyclophosphamide, azathioprine, mycophenolate, glitazones, endothelin receptor antagonists, or Fulvestrant (ICI-182, 780).

The disclosure is illustrated by the following non-limiting Examples.

EXAMPLES

Excessive deposition of extra cellular matrix (ECM) components such as fibronectin (FN) and type I collagen (Col1α1) by organ fibroblasts is defined as fibrosis. Organ fibrosis is the final common pathway for many diseases that result in end-stage organ failure. However, effective therapy for organ fibrosis is still unavailable (see, for example, Bjoraker et al., Am. J. Respir. Crit. Care. Med 2000; 157:199-20; Varga and Abraham, J Clin Invest 2007; 117: 557-67; Wynn, J Clin Invest 2007; 117:524-29). Uncontrollable wound-healing responses, including acute and chronic inflammation, angiogenesis, activation of resident cells, and ECM remodeling, are thought to be involved in the pathogenesis of fibrosis (Wynn, J Clin Invest 2007; 117:524-29; Kalluri and Sukhatme, Curr Opin Nephrol Hypertens 2000;

9:413-8). TGF-β is the prototype fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs) (Branton, Microbes Infect 1999; 1:1349-65; Varga and Pasche Nature Reviews Rheumatology 2009; 5:200-6). Despite high expectations, a clinical trial of a monoclonal anti-TGF-β antibody in patients with early SSc failed to show any efficacy (Varga and Pasche, Nature Reviews Rheumatology 2009; 5:200-6).

Endostatin is a 20-kDa internal fragment of the carboxy-terminus of collagen XVIII. It was originally identified in the supernatant of a cultured murine hemangioendothelioma cell line with potent antiangiogenic activity (O'Reilly et al., Cell 1997; 88:277-85). Endostatin inhibits endothelial proliferation and tube formation in vitro, and tumor growth in vivo (Dhanabal et al., Biochem Biophys Res Commun 1999; 258:345-52). Studies have been conducted to assess endostatin's anti-tumor properties, including clinical trials (Folkman, Exp Cell Res 2006; 312:594-607). The $NH_2$-terminal domain of endostatin has been reported as the functional domain responsible for inhibiting angiogenesis (Tjin Than Sjin et al., Cancer Res 2005; 65:3656-63). Although the exact molecular mechanism of its effect remains unclear, integrins, glypicans, flk-1, and nucleolin have been reported as endostatin receptors (Sudhakar et al., Proc Natl Acad Sci USA 2003; 100:4766-71; Karumanchi et al., Mol Cell 2001; 7:811-22). Recent studies have shown that endostatin is increased in serum and/or BALF obtained from IPF and SSc patients with pulmonary fibrosis (for example, Sumi, J Clin Lab Anal 2005; 19:146-9).

In the studies presented herein, the effects of endostatin on fibrosis were evaluated. The effect of endostatin and endostatin-derived peptides on fibrosis in vitro was assessed using primary human fibroblasts, ex vivo using human skin, and in vivo in mice skin treated with TGF-β. Surprisingly, the findings demonstrate that a carboxy-terminal peptide of endostatin has anti-fibrotic activity and provide a novel therapy for fibrotic disorders.

Example 1

Materials and Methods

Reagents and antibodies. The full-length recombinant human endostatin (rE) was purchased from Sigma-Aldrich (St. Louis, Mo.). Recombinant human TGF-β was from R&D Systems Inc. (Minneapolis, Minn.). Mouse monoclonal anti-human fibronectin (FN) antibody, goat polyclonal anti-human type I Collagen αI chain (Col1α1) antibody, and mouse monoclonal anti-human GAPDH antibody were from Santa Cruz Biotechnology (Santa Cruz, Calif.). Mouse monoclonal anti-human α-smooth muscle actin (α-SMA) antibody was from Sigma-Aldrich.

Synthesis of human endostatin peptides. Peptides were synthesized by the solid-phase on Liberty Microwave Synthesizer (CEM Corporation, 3100 Smith Farm Road, Mathews, N.C. 28106) using FMOC synthesis protocol. Briefly, synthesis was performed by stepwise addition of activated amino acids to the solid support (Wang resin and PEG-PS) starting from the carboxy terminus to the amino terminus. Activation of amino acids was performed by DIPEA/HOBT/TBTU chemistry. At the end of the synthesis, peptides were cleaved off the resin with reagent R (90% TFA, 5% Thioanisole, 3% Ethanedithiol, and 2% Anisole) and subjected to multiple ether extractions. The crude peptides were analyzed, characterized, and purified by Gel filtration (G-25 column), Reversed-Phase High Performance Liquid Chromatography (RP-HPLC, 486 and 600E by Waters Corporation). The correct mass was confirmed by MALDI-TOF Mass Spectroscopy (The Voyager-DE STR Biospectrometry Workstation). Sequences of the peptides are shown in Table 1 and correspond to amino acids 1-45 (E1); 71-115 (E2); 133-180 (E3), 133-180A (E4) which differs from E3 by the presence of a carboxy-terminal amide. The purity of all peptides was >98%. All peptides were dissolved in DMSO at a concentration 5 mg/ml, and diluted in 1×PBS to 1-20 µg/ml. Primary fibroblast culture. Human primary lung and skin fibroblasts were cultured. The explanted lungs of normal organ donors, patients with SSc or IPF, and clinically involved skin of SSc patients, a morphea patient and healthy donors were used for primary fibroblast culture. Approximately 2-cm pieces of peripheral lung and skin were minced and fibroblasts were cultured in Dulbecco's modified Eagle's medium (DMEM; Mediatech, Herndon, Va.) supplemented with 10% FBS, penicillin, streptomycin, and anti-mycotic agent, as previously described (Feghali et al., Arthritis Rheum 1999; 42:1451-7). All the cells were used between passages 3-6.

Western blot analysis. Cellular lysates were obtained from cultured fibroblasts as previously described (Pilewski et al., Am J Pathol 2005; 166:399-407). Briefly, $2.0 \times 10^5$ primary fibroblasts were cultured in 35-mm wells in 0.5% FBS-containing medium supplemented with 10 ng/ml of human recombinant TGF-β or PBS as vehicle control for 24 h, following which 5 µg/ml of human rE, endostatin peptides (E1-E4), or DMSO (vehicle) was added for 48 h. In some experiments, endostatin peptides were used without TGF-β stimulation. Cellular lysates were analyzed by western blot. Signals were detected following incubation with horseradish peroxidase-conjugated secondary antibody and chemiluminescence (Perkin Elmer Life Sciences, Inc., Boston, Mass.). The intensity of individual bands with expected molecular sizes was semi-quantitatively analyzed using the image/J® software available at on the internet (/rsb.info.nih.gov/ij/index.html), and normalized to individual GAPDH intensity.

Ex vivo human skin assays. Human abdominal skin was obtained from corrective plastic surgery. As previously described (Yasuoka et al., The Open Rheumatol J 2008; 2:17-22), subcutaneous fat tissue was removed uniformly and skin tissue was cut into 1.5 cm×1.5 cm sections. The following were injected intradermally in a total volume of 100 µl 1×PBS: rE alone (1-10 µg/ml), endostatin peptides alone (10 µg/ml), rE or endostatin peptides (1-20 µg/ml) in combination with TGF-β (10 ng/ml), and TGF-β alone (10 ng/ml). In some experiments, human skin was first injected with TGF-β for 48 h followed by recombinant endostain (rE) administration in the same injection site as TGF-β. Independent experiments were conducted in duplicate or triplicate as indicated in the figure legends. Explants containing complete epidermal and dermal layers were cultured in an air liquid interface with the epidermal and keratin layers side up and exposed to air. The culture medium was replaced every other day. After 1 or 2 weeks, skin tissue corresponding to an area with 8-mm diameter centered around the injection site was harvested using disposable 8-mm Acu Punch® (Acuderm inc., Lauderdale, Fla.). Skin tissue was fixed in 10% formalin prior to embedding in paraffin.

In vivo mouse experiments. CB57BL6/J male mice were purchased from The Jackson Laboratory (Bar Harbor, Me.). Human rE (10 µg/ml) or Endostatin peptides (10 µg/ml) in combination with TGF-β (10 ng/ml), or TGF-β alone were injected intradermally on the back of mice in a total volume of 100 μl 1×PBS. Mice were injected in two different skin sites and sacrificed one week post-injection. Skin surrounding the injection site was harvested and fixed in 10% formalin prior to embedding in paraffin.

Measurement of Skin Dermal Thickness: Six μm sections of paraffin-embedded human and mouse skin tissues were stained with hematoxylin and eosin (H&E). In some experiments, sections were stained with Masson trichrome which identifies collagens. Images were taken on a Nikon Eclipse 800 microscope. The thickness of the dermis was measured in 6 random fields of each section using the image/J® software. Data are shown in arbitrary units.

Tubular formation assay. The ability of endostatin peptide to inhibit angiogenesis was examined in tubular formation assay using Matrigel® culture. Human umbilical vein endothelial cells (HUVECs) were maintained in endothelial cell basal medium-2 (EBM-2; Clonetics, San Diego, Calif.) supplemented with EBM-2 MV SingleQuots®. HUVECs ($5 \times 10^4$) were cultured in duplicate on 24-well Matrigel® plates (BD Biosciences, San Diego, Calif.) alone, or in the presence of rE or E4 peptide (50 nM) in EBM-2 at 37° C. DMSO was used as vehicle control. After 24 hours, images were captured using a converted microscope. The degree of cord formation was quantified by measuring the area occupied by tubes in 6 random fields per well. Three independent experiments were performed.

Statistical Analysis. All continuous variables were expressed as the mean±standard deviation. Comparisons between 2 groups were tested for statistical significance using the paired t-test or Mann-Whitney U test as appropriate. Comparison among 3 groups was performed using ANOVA followed by Bonferroni's test.

Example 2

Human Endostatin Inhibits FN and Col1al Production in TGF-β-Treated Human Primary Lung and Skin Fibroblasts In Vitro To evaluate whether endostatin modulates production of ECM components in fibroblasts, FN and Col1α1 expression was examined in normal human lung fibroblasts by western blot analysis. Cells were treated with 5 μg/ml rE for 48 h with or without pre-stimulation with human TGF-β for 24 h. As shown FIG. 1A, rE dramatically reduced FN and Col1α1 levels in TGF-β pre-treated fibroblasts. To define the functional domain of endostatin that mediates its inhibitory effect, four different peptides were synthesized corresponding to different regions of endostatin (Table 1).

TABLE I

Amino acid sequence of human endostatin fragments.

E1 (1-45 of SEQ ID NO: 2)
H-$^1$HSHRDFQPVLHLVALNSPLSGGMRGIRGADFQCFQQARAVGLAG
T$^{45}$-OH

E2 (71-115 of SEQ ID NO: 2)
H-$^{71}$IVNLKDELLFPSWEALFSGSEGPLKPGARIFSFDGKDVLRHPTW
P$^{115}$-OH

E3 (133-180 of SEQ ID NO: 2)
H-$^{133}$SYCETWRTEAPSATGQASSLLGGRLLGQSAASCHHAYIVLCIEN
SFMT$^{180}$-OH

E4 (133-180A of SEQ ID NO:2)
H-$^{133}$SYCETWRTEAPSATGQASSLLGGRLLGQSAASCHHAYIVLCIENS
FMT$^{180}$-CONH2

Figure 1B:
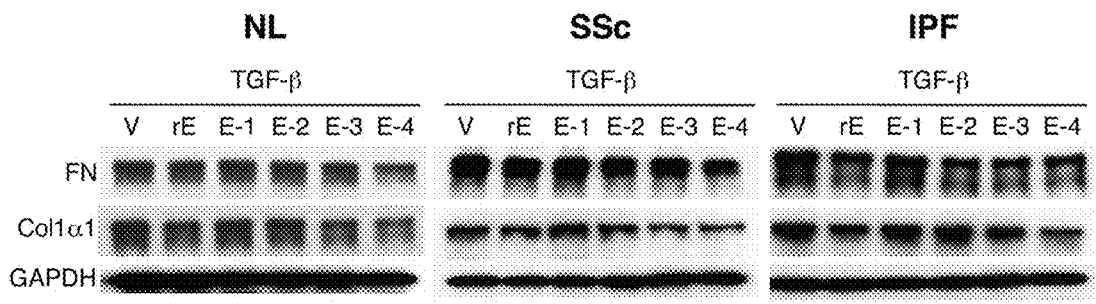
Figure 1C:
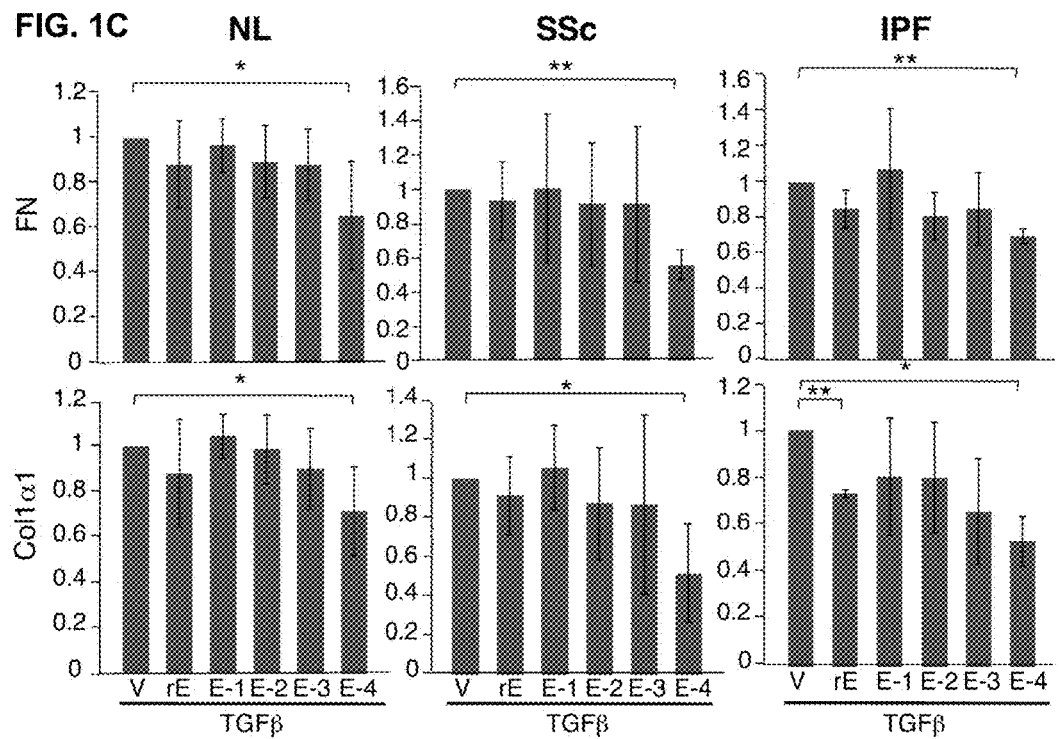
Figure 1D:
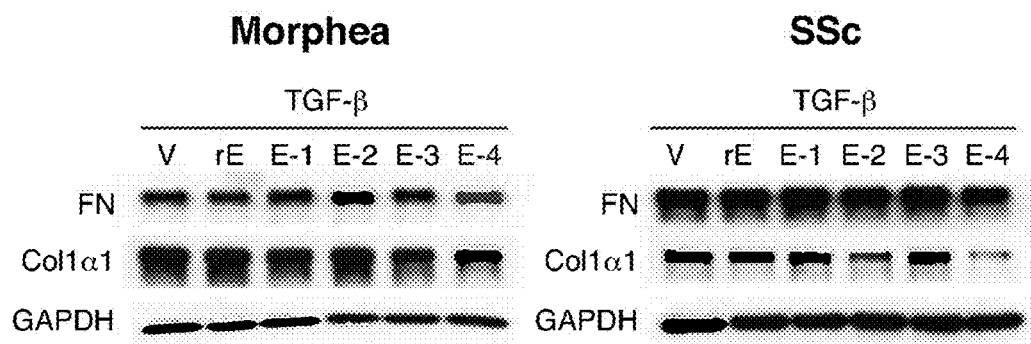

As shown in FIGS. 1B and 1C, a fragment from the carboxy terminus of endostatin (E4) significantly suppressed FN and Col1α1 production in TGF-β treated cells compared with normal lung fibroblasts treated with TGF-β alone (P=0.03, in both comparisons). On the other hand, E1 peptide, located in the amino terminal region of endostatin, had no effect. In addition to healthy fibroblasts, lung fibroblasts obtained from SSc and IPF patients, who had clinical lung fibrosis, were used in parallel assays with similar results (FIGS. 1B and 1C). Having demonstrated antifibrotic effects of rE and E4 in lung fibroblasts, the effects of these peptides was examined on skin fibroblasts since skin is a major organ affected by fibrosis in SSc. Primary fibroblasts obtained from the skin of healthy controls, patients with systemic sclerosis (SSc) or localized scleroderma (morphea) were treated with rE or E4. Similarly to lung fibroblasts, rE and E4 reduced TGF-β-induced ECM production in dermal fibroblasts. Representative results are shown in FIG. 1D.

Example 3

Figure 1E:
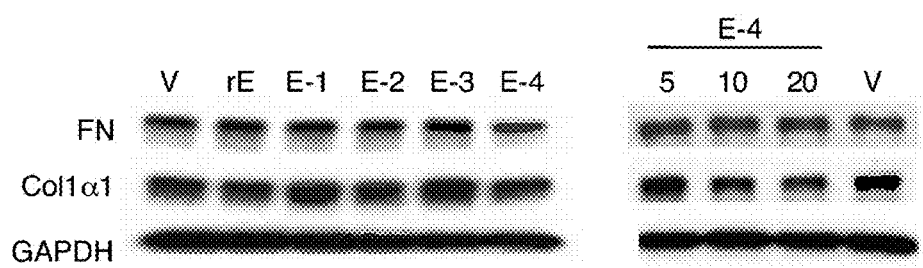

Endostatin Peptides Reverse the Fibrotic Phenotype of Primary Lung Fibroblasts from Patients with SSc and IPF Since it has been shown that TGF-β is upregulated in fibrotic tissue, it was examined if matrix production in fibrotic lung fibroblasts was altered by treatment with endostatin peptide in the absence of TGF-β stimulation. As shown in FIG. 1E left panel, both FN and Col1α1 levels decreased in E4-treated fibroblasts. In addition, the same fibroblasts were treated with different concentrations of E4 to identify the optimal anti-fibrotic dose. E4 dose-dependently reduced Col1α1 levels when compared to vehicle control (FIG. 1E, right panel), but had a modest effect on FN levels. The reduction in ECM was more modest than that observed following TGF-β stimulation. Taken together, the results indicate that E4 can reduce baseline production of ECM components in fibroblasts from a fibrotic milieu and thus reverse the fibrotic phenotype.

Figure 1F:
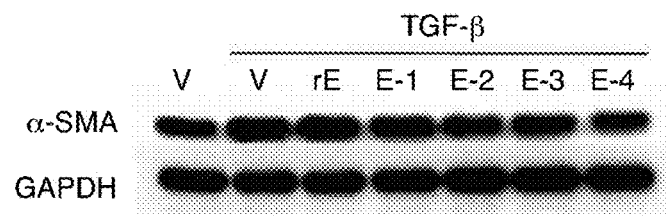

Myofibroblasts, activated fibroblasts which express α-SMA, are induced by TGF-β stimulation and play a central role in fibrosis. Therefore, the effects of endostatin peptides on α-SMA expression in normal lung fibroblasts was examined. As shown in FIG. 1F, TGF-β stimulation greatly increased α-SMA expression. Interestingly, E4, and to a lesser extent E3, decreased TGF-β-induced α-SMA levels suggesting that the carboxy-terminal region of endostatin can prevent the activation of fibroblasts and their transition to a myofibroblastic phenotype.

Example 4

Figure 2A:
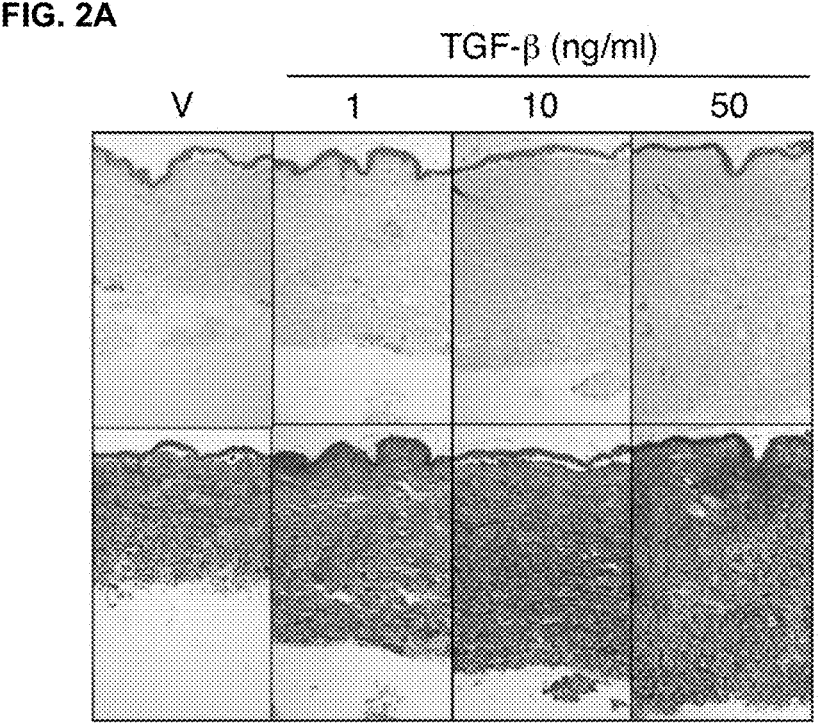
FIGS. 2A-2C. Ex vivo human skin fibrosis organ culture model. A: Recombinant TGF-β or 1×PBS (vehicle) was injected intradermally into human skin explants at a concentration of 1, 10, 50 ng/ml. Skin was harvested 1 week post-injection. Representative H&E images are shown in the upper row, and images of Masson trichrome-stained section are shown in the lower row. Magnification, 20×. B: Recombinant endostatin (rE) was injected into human skin at a concentration of 1, 5, 10 μg/ml. 1×PBS was used as a vehicle control (V). Representative H&E images are shown. Magnification, 20×. C: Endostatin polypeptides (E-1, E-2, E-3, and E-4; all at 10 μg/ml) were injected intradermally in human skin. DMSO was used as a vehicle control (V). Representative H&E images are shown. Magnification, 20×.
Figure 2B:
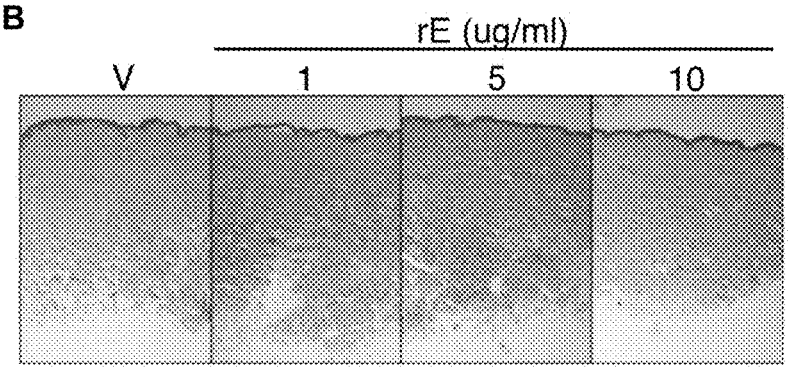
Figure 2C:
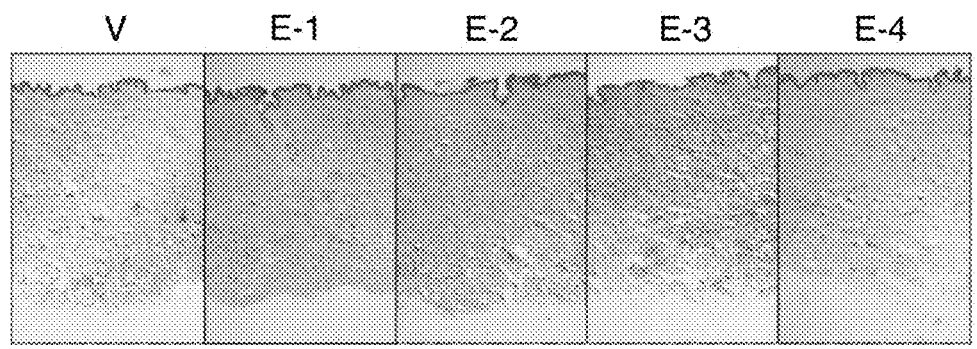
Figure 3A:
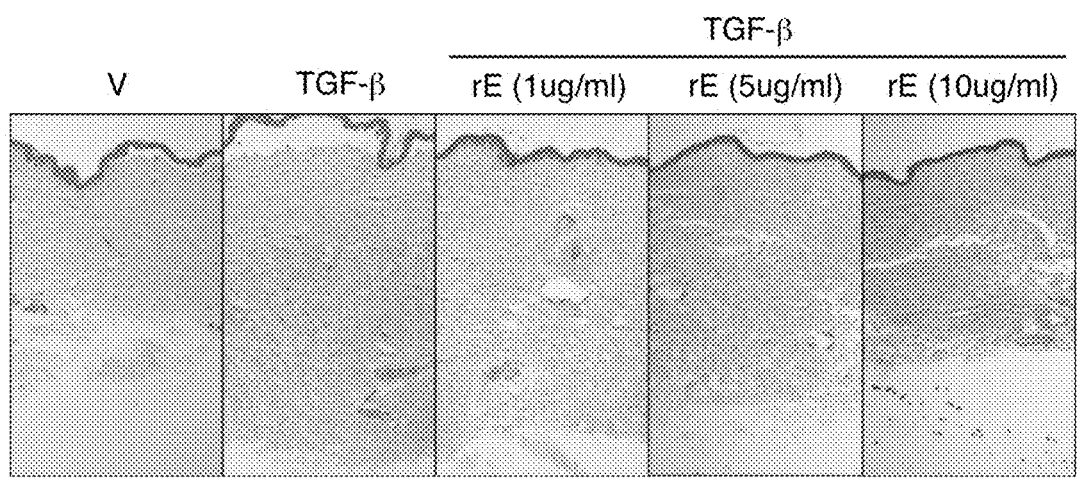
FIGS. 3A-3B. The effect of recombinant endostatin on TGF-β-induced fibrosis and dermal thickness in human skin. A: Representative H&E images of human skin injected with Vehicle, 10 ng/ml TGF-β alone, or rE, (1, 5, and 10 μg/ml) in combination with TGF-β (10 ng/ml). Tissues were harvested one week post-injection. Magnification, 20×. B: Graphical presentation of dermal thickness. Data represent four independent experiments in triplicate using human skin explants from four different donors. Mann-Whitney U test was used for statistical analysis. * P<0.04.
Figure 3B:
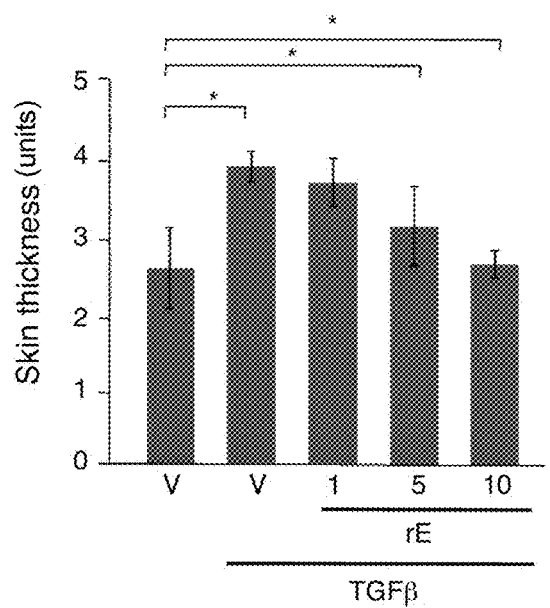

Endostatin Reduces Dermal Thickness and Prevents TGF-β-Induced Fibrosis in Human Skin Cultured human skin explants can be used as an organ model to assess the effects of fibrogenic factors and for evaluating the efficacy of inhibitors/therapies to halt the progression of fibrosis and potentially reverse it (Yasuoka, The Open Rheumatol J 2008; 2:17-22). To evaluate the efficacy of endostatin as a potential therapeutic agent for fibrosis, this ex vivo human skin model was used. Since TGF-β is a well-known pro-fibrotic factor that plays a central role in fibrosis, human recombinant TGF-β was first injected intradermally to assess the level of fibrosis. As shown in FIG. 2A, TGF-β injection dramatically increased dermal thickness in a dose-dependent manner one week post-injection. The fibrotic effect of TGF-β (10 ng/ml) resolved by two weeks. The baseline effects of rE (1, 5, and 10 µg/ml) or endostatin peptides (10 µg/ml) were also examined individually. Although rE and E1-4 did not significantly alter dermal thickness, rE, E3, and E4 showed a tendency towards reduction in human dermal thickness (FIGS. 2B and 2C). It was determined if rE could inhibit fibrosis in TGF-β-treated human skin. TGF-β and rE were injected simultaneously. One week post-administration, rE in combination with TGF-β significantly reduced dermal thickness in a dose-dependent manner (FIG. 3). To assess the effects of rE on reversing fibrosis, the peptide was injected 2 days after TGF-β administration. Similarly to co-treatment, delayed rE also significantly ameliorated TGF-β-induced dermal fibrosis. The findings indicate that human endostatin can prevent the development and progression of fibrosis and also reverse TGF-β-induced fibrosis in human skin.

Example 5

Figure 4A:
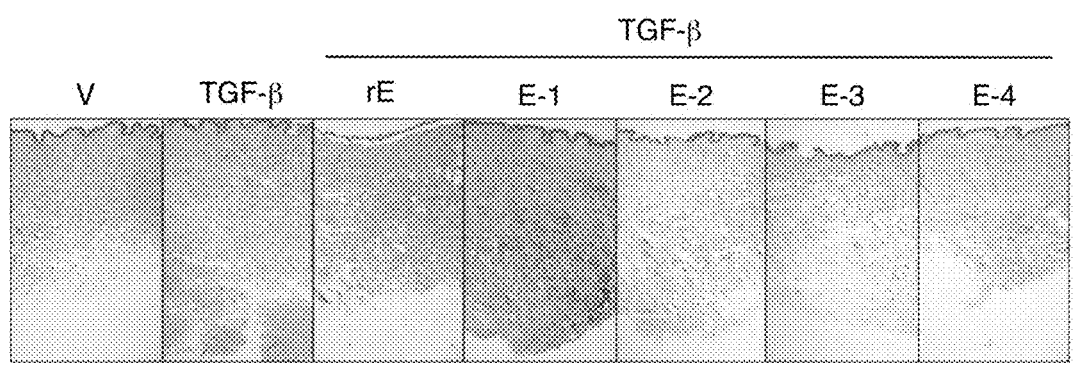
FIGS. 4A-4B. The effect of endostatin polypeptides TGF-β-induced fibrosis and dermal thickness in human skin. A: Representative H&E images of human skin injected with Vehicle, 10 ng/ml TGF-β alone, or E-1, E-2, E-3, or E-4 (10 μg/ml) in combination with TGF-β (10 ng/ml). Magnification, 20×. B: Graphical presentation of dermal thickness data shown in A. Data represent two independent experiments using human skin explants from two donors, and each experiment was done in triplicate Mann-Whitney U test was used for statistical analysis. * P<0.05, ** P<0.02.
Figure 4B:
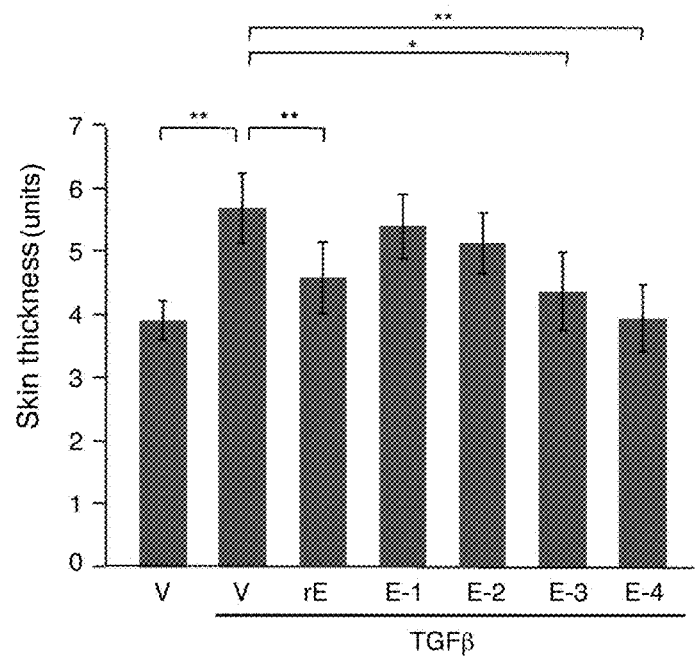
Figure 5A:
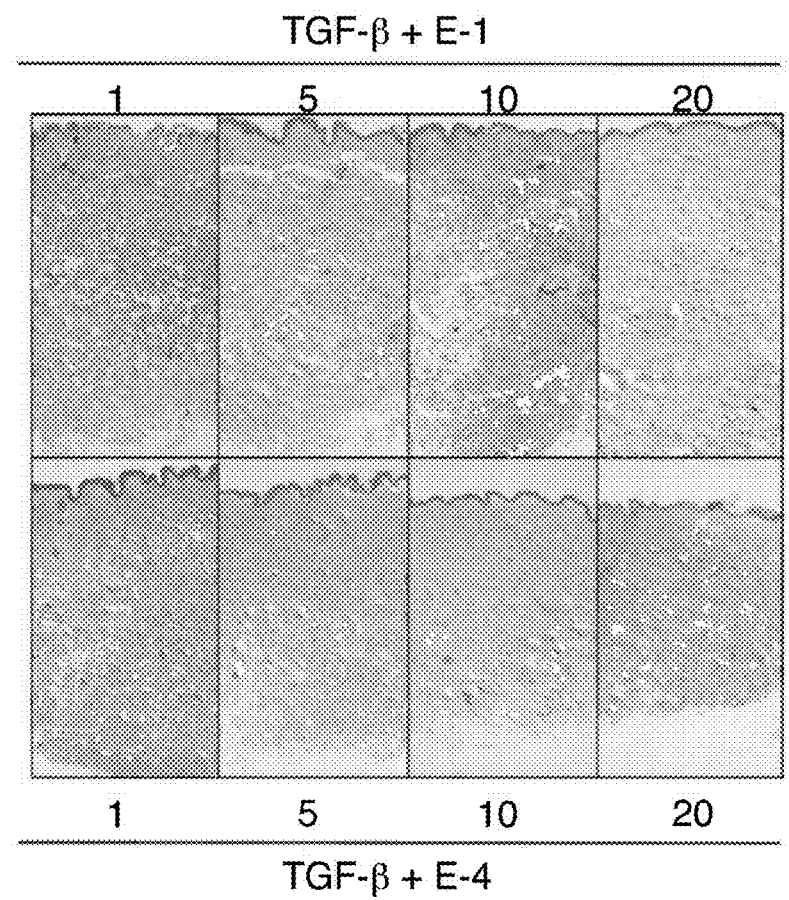
FIGS. 5A-5B. Dose response of E-1 and E-4 in TGF-β-induced fibrosis. A: Representative H&E images of human skin injected with E-1 (upper row) or E-4 (lower row) at a concentration of 1, 5, 10, and 20 μg/ml in the presence of TGF-β (10 ng/ml). Magnification, 20×. B: Graphical analysis of dermal thickness data shown in A. DMSO was used as a vehicle control. Experiments were conducted in duplicate, and dermal thickness was measured in 6 fields from each section. Mann-Whitney U test was used for statistical analysis. * P<0.02, ** P<0.01.
Figure 5B:
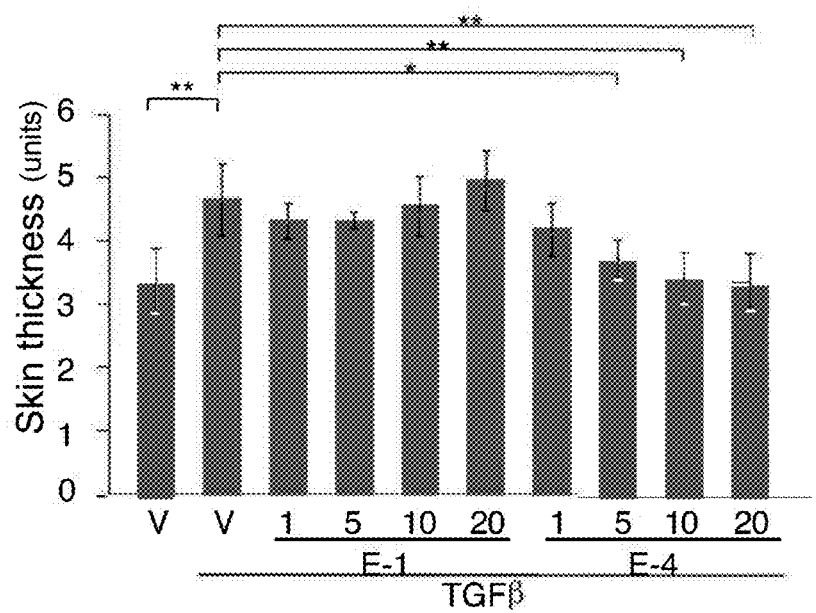
Figure 17A:
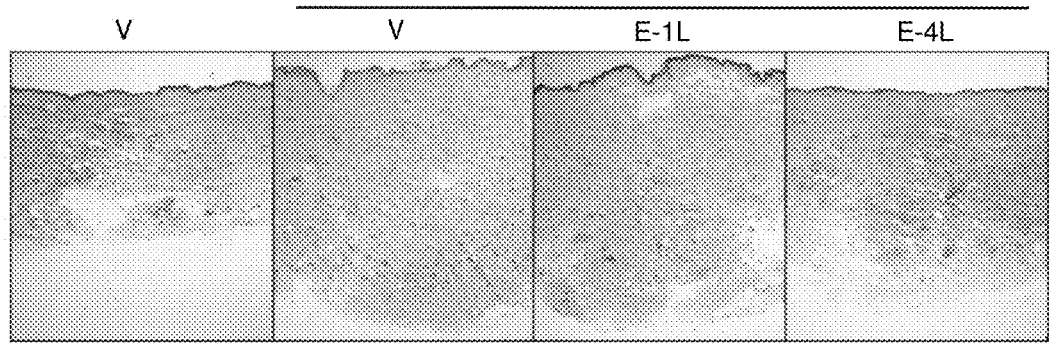
FIG. 17A-17B. The effect of endostatin peptides on established fibrosis triggered by TGF-b in human skin. A: Vehicle (DMSO), E-1, or E-4 (10 mg/ml) was additionally injected to human skin 2 days post-administration of 10 ng/ml TGF-b (V, E-1L and E-4L, respectively). Representative H&E images of human skin were shown. Magnification, 20×. B: Graphical presentation of dermal thickness data shown in A. Data represent two independent experiments using human skin explants from two donors, and each experiment was done in duplicate. Mann-Whitney U test was used for statistical analysis. * P<0.01.
Figure 17B:
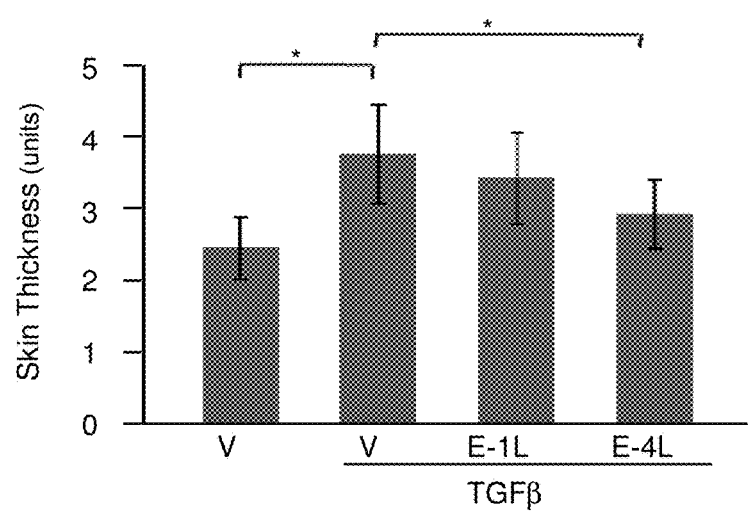

Endostatin Peptides Reduce TGF-β-Induced Fibrosis in Human Skin Ex Vivo and Reverse Existing Fibrosis To determine which part of endostatin is responsible for inhibiting TGF-β-induced fibrosis in human skin explants, endostatin peptides (10 µg/ml) were administrated in the presence of 10 ng/ml of TGF-β. Representative images are shown in FIG. 4A. E3 and E4 significantly abolished the development of fibrosis as measured by dermal thickness when compared to TGF-β alone (P=0.04, 0.01, respectively; FIG. 4). The dermal thickness of skin explants injected with different concentrations of E1 or E4 in combination with TGF-β was examined As shown in FIG. 5, unlike E1, E4 at concentrations of 5-20 µg/ml clearly ameliorated TGF-β-induced skin fibrosis, indicating that the C-terminus of endostatin can suppress fibrosis (see FIG. 17).

Example 6

Endostatin Peptides Reduce TGF-β-Induced Fibrosis In Vivo in Mouse Skin

Figure 6A:
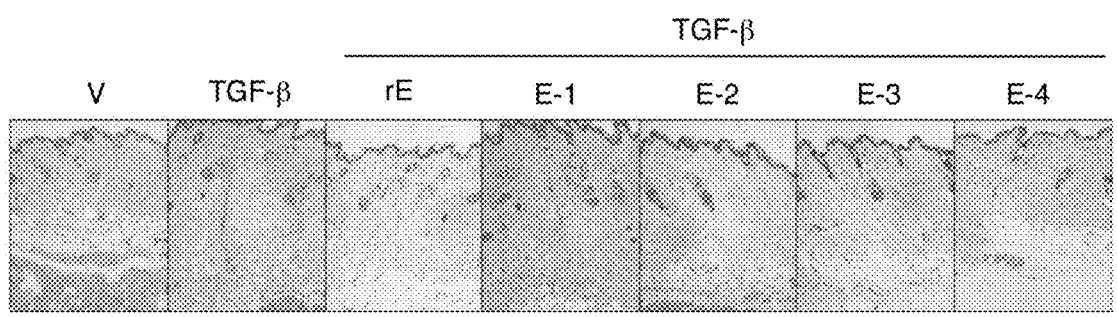
FIGS. 6A-6B. The effect of endostatin polypeptides in the development of fibrosis in vivo in mouse skin. A: Mice were injected intradermally with vehicle, 10 ng/ml TGF-β alone, or E-1, E-2, E-3, and E-4 (10 μg/ml) in combination with TGF-β (10 ng/ml). Skin was harvested after 1 week post-injection. Sections were stained with H&E. Magnification, 20×. B: Graphical summary of dermal thickness data shown in A. Data represent four independent experiments, each done in duplicate. Mann-Whitney U test was used for statistical analysis. * P<0.04, ** P<0.01.
Figure 6B:
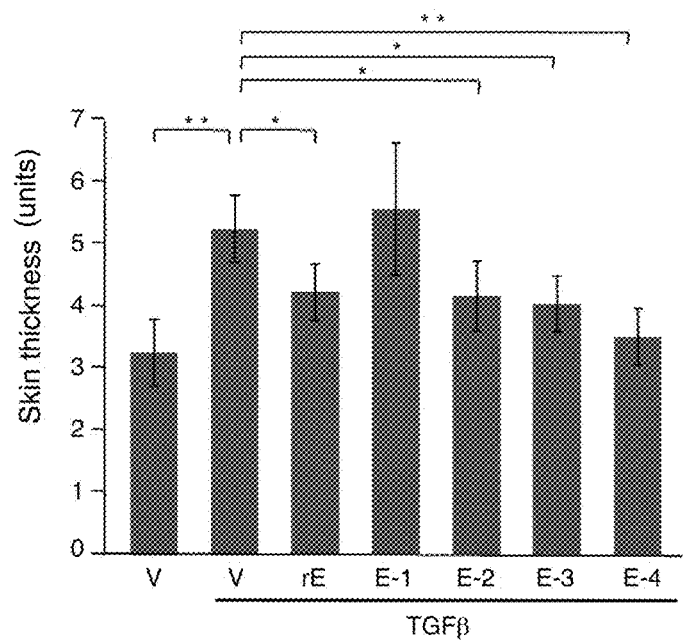

The anti-fibrotic effect of endostatin peptides was further assessed in vivo. rE and endostatin peptides in combination with TGF-β were injected in the skin of mice. One week post-injection, mice appeared healthy and showed no signs of distress. As shown in FIG. 6, human TGF-β strongly increased dermal thickness in mouse skin (P=0.004). Peptides E3 and E4 from the carboxy terminus of human endostatin peptide prevented dermal fibrosis induced by TGF-β (P=0.01, 0.007, respectively). In addition, E2 significantly reduced dermal thickness (P=0.03). E1, a peptide corresponding to the amino terminus of endostatin did not alter TGF-β-induced dermal fibrosis. These results confirmed those obtained in our human skin model and emphasize the importance of the C-terminal domain of endostatin in preventing TGF-β-induced fibrosis in vivo and ex vivo.

Example 7

The C-Terminal Peptide of Endostatin has Modest Anti-Angiogenic Activity

Figure 7A:
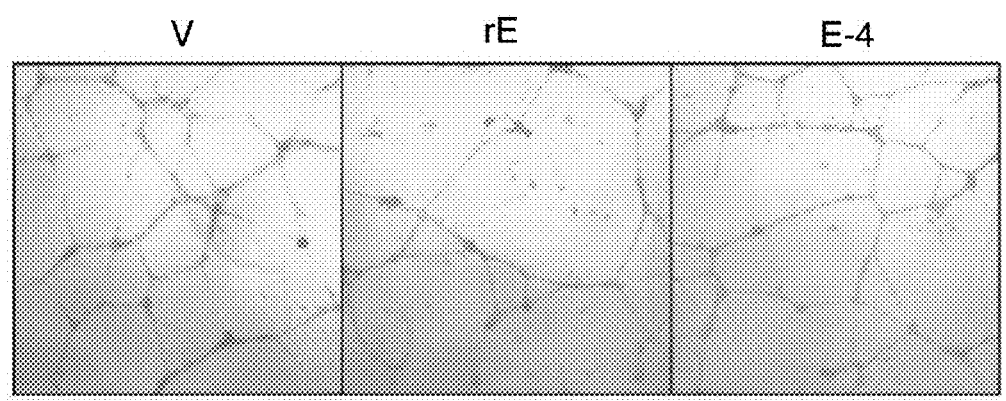
FIGS. 7A-7B. Capacity of endostatin polypeptide to inhibit tubular formation in Matrigel®. A, Representative images of Matrigel® cultures of HUVECs treated with vehicle, rE (50 nM), or E4 (50 nM). An equivalent amount of DMSO was used as vehicle. Magnification 40×. B, Image quantification of the cord formation shown in A. Data shown summarize results of three independent experiments. * P<0.05, one-way ANOVA followed by Bonferroni's test.
Figure 7B:
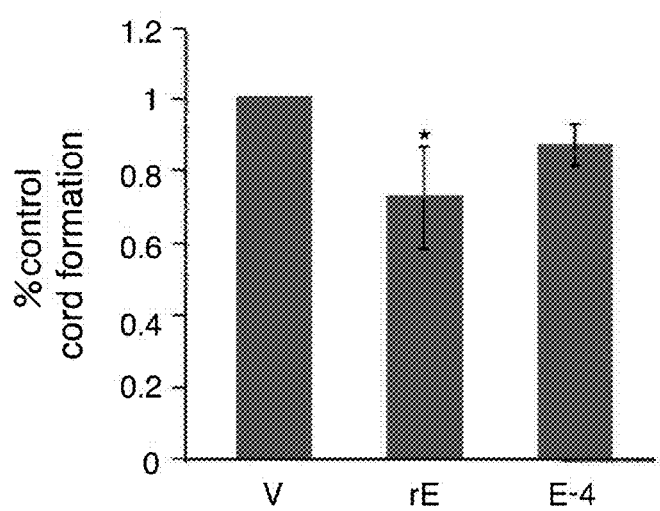

The anti-angiogenic effect of endostatin has been attributed to its amino terminal domain (Tjin Tham Sjin et al., Cancer Res 2005; 65:3656-63). To evaluate the anti-angiogenic capacity of the carboxy terminal regions of endostatin, the effect of E4 on in vitro tubular formation was examined using Matrigel. As shown in FIG. 7, the capacity of rE to inhibit tubular structure formation by HUVECs was significant, confirming previous reports. On the other hand, the ability of E4 to suppress angiogenesis was modest, suggesting that the region of endostatin corresponding to E4 does not significantly contribute to its anti-angiogenic activity.

Thus, E4, a peptide corresponding to the carboxy terminal region of endostatin, ameliorates TGF-β-induced fibrosis and even reverses it. E4 suppressed TGF-β-induced ECM production and downregulated α-SMA levels in primary lung and skin fibroblasts. In vivo and ex vivo analyses revealed that E4 impedes the increase of skin dermal thickness triggered by TGF-β. Furthermore, the anti-angiogeneic capacity of E4 was low compared to that of rE. Taken together, the findings suggest that the domains of endostatin responsible for its anti-fibrotic and anti-angiogenic capacity are distinct. Other endostatin peptides (for example, E2 and E3) are shown to have anti-fibrotic activity.

The anti-angiogenic activity of endostatin has been the focus of numerous investigations directed at the development of anti-tumor therapy. Recently, elevated serum and BALF levels of endostatin in fibrotic disorders such as idiopathic pulmonary fibrosis (IPF) and systemic sclerosis (SSc) were reported. Endostatin levels were relatively increased in IPF patients with severe respiratory dysfunction and in SSc patients with pulmonary fibrosis, severe skin fibrosis, and with cutaneous scars, compared to patients without those clinical manifestations (Sumi J Clin Lab Anal 2005; 19:146-9; Richter et al., Thorax 2009; 64:156-61). In addition, collagen XVIII expression was increased in cultured dermal fibroblasts of SSc patients (Tan et al., Arthritis Rheum 2005; 52:865-76) and in whole lung extracts of patients with IPF (Yang et al., Am J Respir Crit Care Med 2007; 175:45-54). In this regard, since endostatin is a proteolytic product of collagen XVIII cleaved by several proteases including MMPs and cathepsin L (Wen e al., Cancer Res 1999; 59:6052-6; Felbor, EMBO J 2000; 19:1187-94), and since MMPs are also upregulated in SSc and IPF (Richter et. al., Thorax 2009; 64:156-61, Toubi et al., Clin Exp Rheumatol 2002; 20:221-4), the observations that cleaved endostatin levels are elevated in those patients is plausible. However, it is unclear how endostatin may be involved in the pathogenesis of fibrosis.

Without being bound by theory, increased endostatin in fibrotic tissues may constitute a negative feedback regulatory loop which, although unsuccessful, is directed at halting the progression of fibrosis. Since endostatin was originally identified in aberrant "angiogenic" endothelial cancer cells as a product that likely controls/inhibits its "angiogenic" capacity (O'Reilly et al., Cell 1997; 88:277-85), it is plausible that endostatin in fibrosis serves a similar regulatory function.

Bloch W et al reported reduced connective tissue but normal vessel density in recombinant endostatin-treated mouse skin using a wound healing model (Bloch et al., FASEB J 2000; 14:2373-6). Furthermore, a peptide from the N-terminal region of endostatin prevented the progression of peritoneal sclerosis in a mouse model (Tanabe et al., Kidney Int 2007; 71:227-38); the peptide under investigation corresponded to the N-terminus of endostatin encompassing amino acids 1-27.

In contrast, the C-terminal region of endostatin, but not the N-terminus, is shown herein to be responsible for its anti-fibrotic effects. In fact, the peptide corresponding to the N-terminal domain of endostatin contributed to the fibrotic phenotype in some of the assays. Studies directed at defining the specific amino acid sequence responsible for endostatin's anti-angiogenic capacity (Richter et al., Thorax 2009; 64:156-61; Cattaneo et al., Exp Cell Res 2003; 283:230-6; Xu et al., Curr Protein Pept Sci 2008; 9:275-83) have shown that the entire angio-suppressive activity of endostatin was located in a 27-amino-acid peptide in the N-terminal domain (Richter et al., Thorax 2009; 64:156-61). Thus, the functional domain of endostatin that mediates its anti-fibrotic activity is different from that responsible for its anti-angiogenic capacity, implying different mechanisms for inhibiting angiogenesis and fibrosis. The anti-fibrotic C-terminal endostatin polypeptides disclosed herein are therefore capable of selectively inhibiting fribrosis without inhibiting angiogenesis. The C-terminal endostatin polypeptides can be used to more specifically and selectively target unwanted fibrosis without interfering with angiogenesis that may impact a desired therapeutic outcome.

The C-terminal endostatin polypeptide also reduces α-SMA expression in TGF-β-treated fibroblasts. In addition, the matrix reducing effects of E4 on normal fibroblasts was modest compared to that in fibrotic fibroblasts. This suggests that the therapeutic effect of endostatin C-terminal peptide in fibrosis could be due, in part, to hindrance of fibroblast activation by TGF-β and other fibrosis promoting growth factors.

In 2005, ENDSTAR®, a recombinant human endostatin purified from *E. coli* containing an additional nine-amino acid sequence produced as a his-tagged protein was approved for the treatment of non-small-cell lung cancer in China (Sun et al., J Clin Oncol 2005 (ASCO Annual meeting proceedings); 23:7138). Despite its effectiveness, the treatment had several disadvantages including a requirement for high doses, the protein's short half-life, poor stability and easy inactivation (see, for example, Crystal, Nat Biotechnol 1999; 17:336-7; Hu et al., Acta Pharmacol Sin 2008; 29:1357-69). The small synthetic peptides disclosed herein could overcome these obstacles. E4 significantly inhibited fibrosis compared to rE and even E3 in vitro, in vivo, and ex vivo. In addition, E4 had minimal anti-angiogenic activity compared to rE, confirming that the anti-angiogenic activity of endostatin resides in its N-terminal domain. The only difference between E3 and E4 was the presence of an amide-bond in the C-terminus of E4. Without being bound by theory, this amide renders the peptide more resistant to carboxy degradation by carboxypeptidases or other degrading molecules, thus stabilizing the peptide and likely maintaining its biological activity (Yang et. al. Am J Respir Crit Care Med 2007; 175:45-54).

Unfortunately, there are no effective therapies for organ fibrosis. The C-terminal domain of endostatin, corresponding to amino acid sequence 133-180 with amide-bond formation, suppressed ECM production by primary skin and lung fibroblasts and ameliorated dermal fibrosis induced by TGF-β in vivo and ex vivo in human skin. The findings presented herein demonstrate that E4 could be used for the treatment of fibrotic disorders, including IPF, SSc, morphea, as well as Graft-versus-host disease, keloid and hypertrophic scar, and other organ fibrosis such as subepithelial fibrosis in asthma.

Example 8

Confirmation of the Efficacy of E4

E4, a peptide representing the carboxy terminus of human endostatin, can attenuate fibrosis triggered by multiple fibrogenic factors. The anti-fibrotic effects of E4 can be detected whether administered concomitantly with or following the fibrogenic trigger. The efficacy of E4 was confirmed in four pre-clinical models of fibrosis: a) bleomycin-induced dermal fibrosis in vivo in mouse skin, b) TGF-β induced dermal fibrosis in mouse skin, and c) bleomycin-induced pulmonary fibrosis. E4 peptide or a control peptide (E1; representing the amino terminal region of endostatin) were administered at the same time as TGF-β or bleomycin or 3-4 days following TGF-β or bleomycin. Mice were sacrificed one and two weeks after TGF-β-initiation of dermal fibrosis, and two and three weeks after bleomycin-induced pulmonary fibrosis. Two different modes of administration of the E4 peptide were also tested. It was confirmed that intraperitoneal and intratracheal administration was effective. The amount of E4 that was administered ws 10 μg/ml in a total volume of 100 μl for skin and IP injections and 50 μl for IT administration.

For these studies, fibrosis was assessed by measurement of dermal thickness on H&E skin sections (skin), assessment of collagen levels by Masson Trichrome staining (skin and lung), and measurement of collagen levels by Sircol assay (lung). Furthermore, to confirm the mechanism by which E4 exerts its anti-fibrotic effects, the production of extra-cellular matrix (ECM) components, the levels of enzymes that promote matrix stabilization and thus accumulation and levels of those that degrade ECM components, and levels of transcription factors downstream of the pro-fibrotic triggers were evaluated. Results were assessed using the unpaired t test and the 3-way ANOVA (for the ID1 data).

Results

E4 caused a significant attenuation of bleomycin induced dermal fibrosis even with a single administration of E4 (FIG. 8). E4 caused a significant decrease of TGFbeta induced dermal fibrosis on day 7. Thus E4 prevents (FIG. 8) and reverses (FIG. 9) dermal fibrosis triggered by TGFbeta.

Figure 10A:
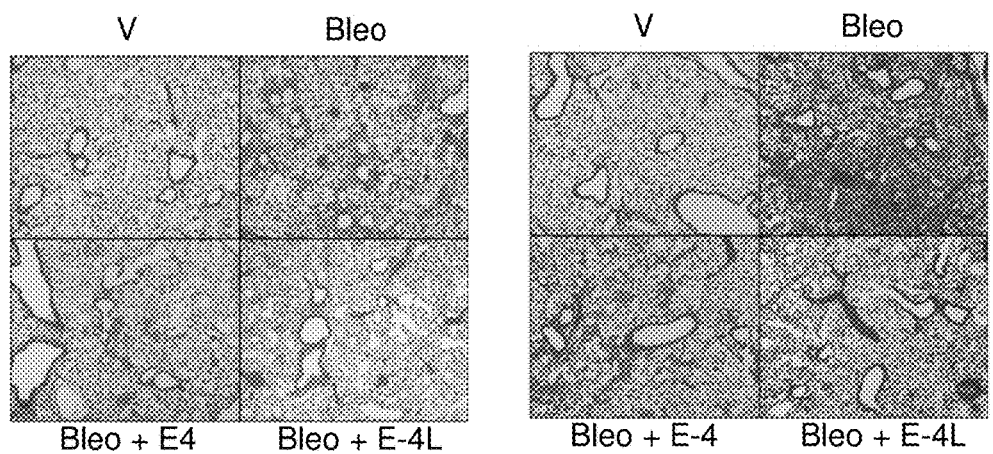
Figure 10B:
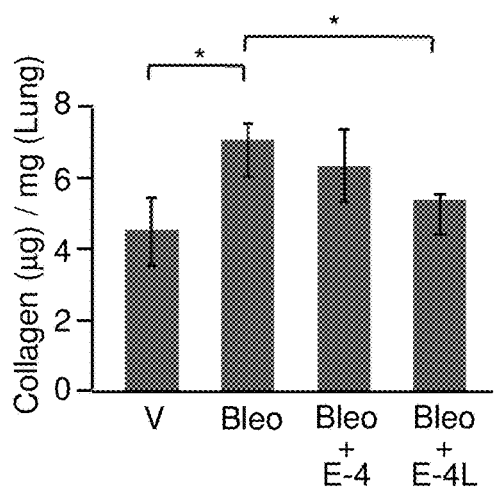

E4 administered concomitantly with bleomycin or three days following bleomycin caused a marked reduction in fibrosis and Masson Trichrome staining (see FIG. 9 and FIG. 10). E4 peptide given three days after bleomycin significantly reduced collagen levels in mouse lungs (FIG. 10, panel B).

Figure 11:
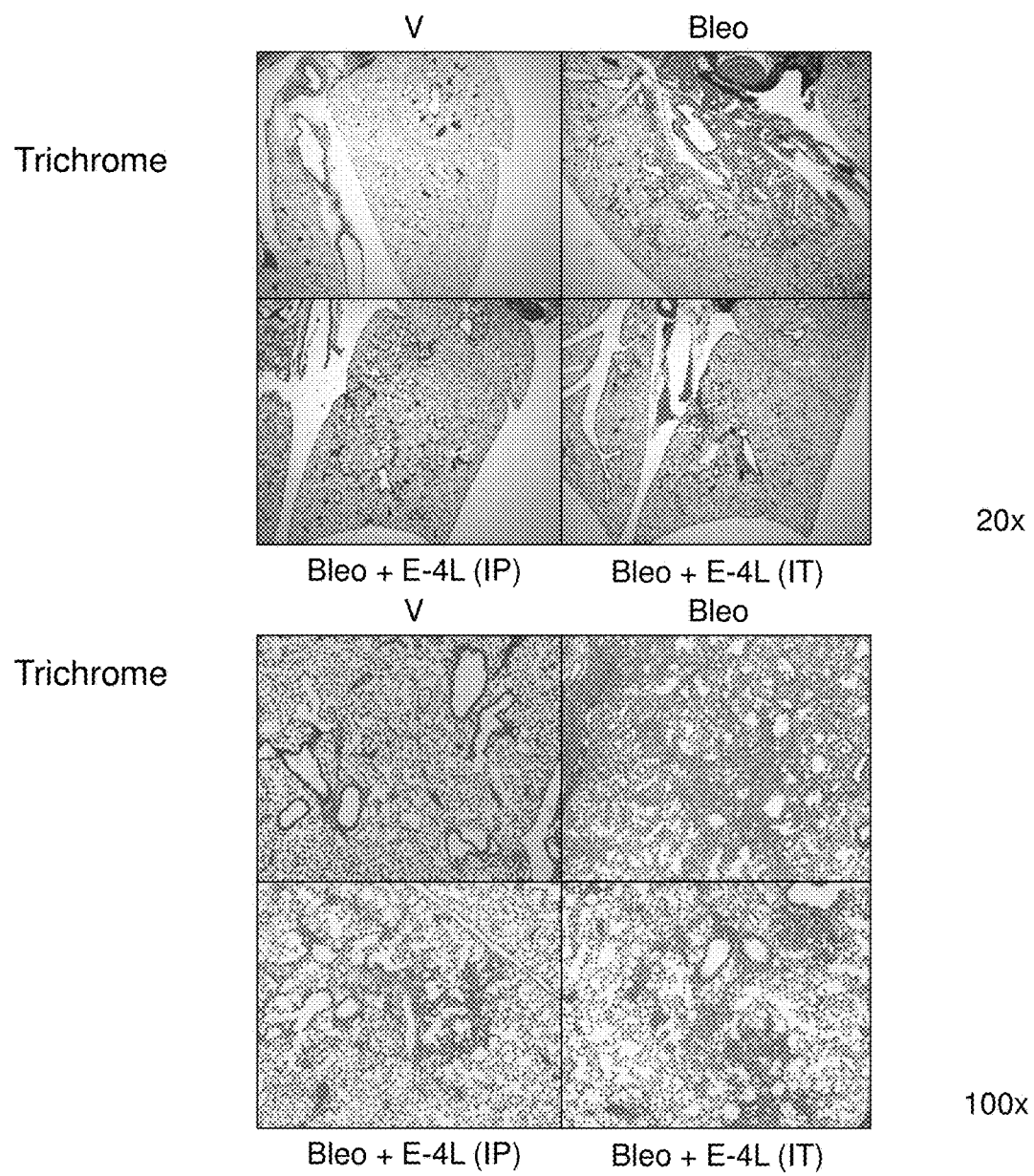
FIG. 11. E4 attenuates bleomycin induced lung fibrosis in vivo whether administered intraperitoneally (IP) or intratracheally (IT). Bleomycin was administered IT at day 1, and E4 was administered either IP or IT at day 3. Lungs were harvested at day 21. E4 caused a significant attenuation of bleomycin induced lung fibrosis on day 21 whether administered IP or IT. Thus E4 is effective at reducing fibrosis irrespective of the route of administration. Results are shown for vehicle alone (V), bleomycin alone (Bleo), bleomycin and E4 administered IP, and bleomycin and E4 administered IT.

E4 caused a statistically significant reduction in both TGFβ and bleomycin induced skin (FIG. 8) and lung fibrosis (FIG. 10) regardless of the mode of administration. Intraperitoneal and intratracheal administration of E4 were both effective in blocking dermal and pulmonary fibrosis. For example, E4 caused a significant attenuation of bleomycin induced lung fibrosis on day 21 whether administered intraperitoneally or intratracheally (FIG. 11). Thus E4 is effective at reducing fibrosis irrespective of the administration mode.

Figure 12:
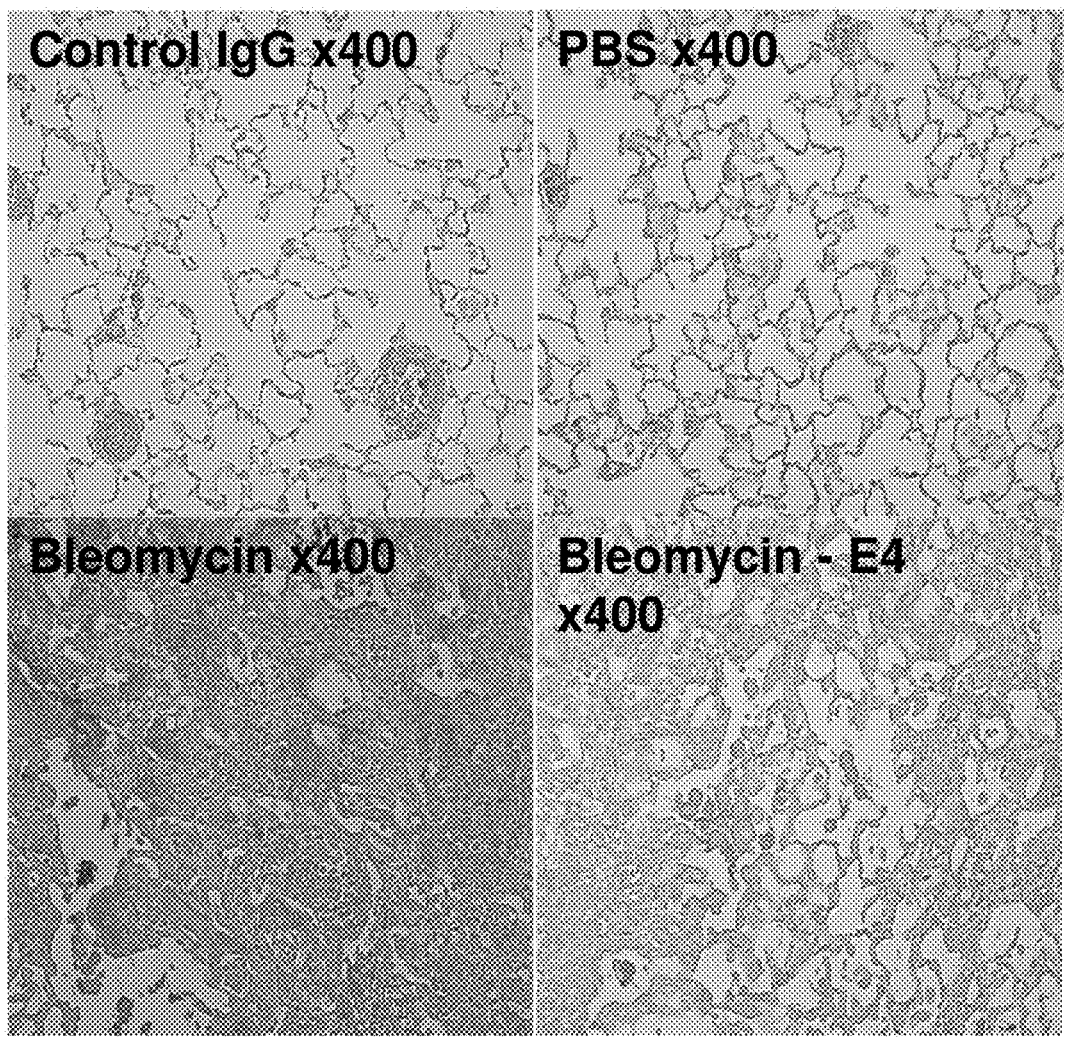
FIG. 12. E4 reduces fibrosis in vivo by reducing levels of lysyl oxidase (LOX), thus reducing crosslinking of collagen and rendering it less stable and more susceptible to proteolytic degradation. Lung sections of mice treated with BLM with or without E4 were used in immunohistochemistry to detect LOX. The sections shown are control IgG, phosphate buffered saline, bleomycin and bleomycin followed by treatment with E4.

The results also evidenced that E4 exerts its anti-fibrotic effects via multiple pathways. E4 reduces levels of lysyl oxidase (LOX), and enzyme responsible for the cross-linking of collagen, elastin, and other extracellular matrix (ECM) molecules and thus the stabilization of the ECM. E4 can make collagen less stable and more susceptible to proteolytic degradation. FIG. 12 shows lung sections of mice treated with bleomycin with or without E4.

Figure 13:
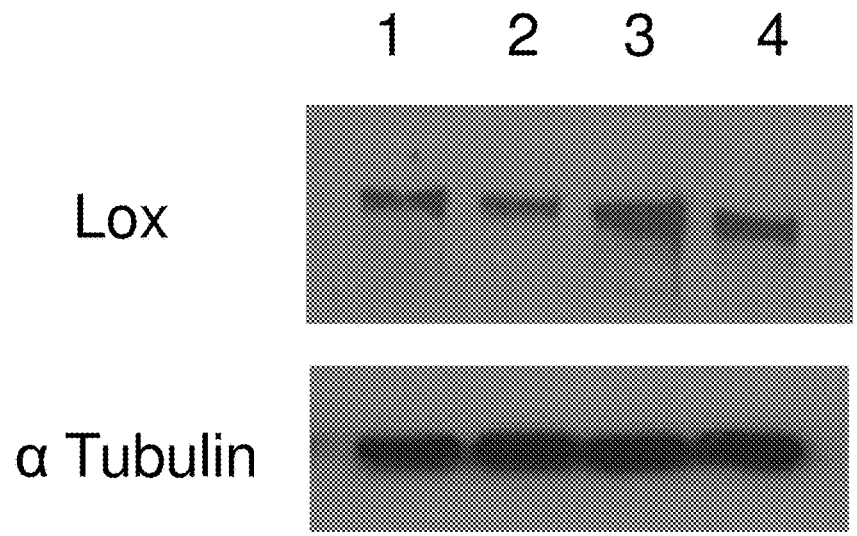
FIG. 13. E4 reduces fibrosis in vitro by blocking TGFβ-induced LOX production in primary human lung fibroblasts. Normal lung fibroblasts in passage 4 were treated with vehicle, E4, TGFbeta, or TGFbeta followed 30 min. later by E4. Media conditioned by the fibroblasts were analyzed using Western blot analysis after 48 hour. Lane 1: Vehicle (DMSO); Lane 2: E-4; Lane 3: TGF β; Lane 4: TGF β followed by E4. Similar results were obtained when LOX mRNA levels were examined by real-time PCR.
Figure 14A:
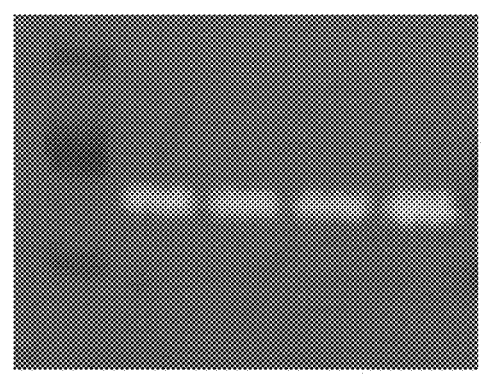
FIG. 14A-14B. A. E4 reduces fibrosis in vitro by inducing MMP-2 activity in primary human lung fibroblasts, thus resulting in increased degradation of collagen and other matrix proteins. Digital image of a gelatin zymography gel showing increased MMP-2 activity when primary human lung fibroblasts are treated with E-4 following TGFβ (lane 4). Lane 1: Vehicle (DMSO); Lane 2: E-4; Lane 3: TGF β; Lane 4: TGF β followed by E4. B. Digital image showing that both total and active MMP-2 levels are increased in cells treated with TGFbeta and E-4. This suggests E-4 increases levels of MMP-2 pro-enzyme, but also increases levels of active matrix metalloproteinase (MMP-2, also called metalloprotease-2).
Figure 14B:
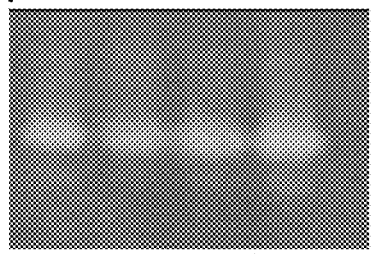

E4-mediated reduction of LOX was detected also was detected in vitro. Normal lung fibroblasts in passage 4 were treated with vehicle, E4, TGFβ, or TGF-β followed 30 minutes later by E4 (FIG. 13). Media conditioned by the fibroblasts were analyzed using western blot analysis after 48 hrs. Treatment with E4 significantly reduced the level of LOX. Similar results were obtained when LOX mRNA levels were examined by real-time PCR E4 also promotes the degradation of ECM components via induction and activation of matrix metalloprotease (MMP-2), an enzyme that degrades several ECM molecules including fibronectin and native and denatured collagens (FIG. 14). In addition, E4 increases levels of inhibitor of differentiation (ID)-1, a transcription factor that inhibits TGF-β effects (see FIG. 15). It was determined in a Western bloat analysis that E4 reduces the levels of the master switch transcription factor, Egr-1 (see FIG. 16) in primary human lung fibroblasts, treated and harvested after 24 hours. The reduction of Egr-1 levels parallels a reduction in collagen, SMA and fibronectin. Egr-1 is known to mediate the effects of several fibrotic agents (including TGF-β and bleomycin).

Thus, E4 exerted significant anti-fibrotic effects. This peptide significantly attenuates the fibrogenic effects of TGFbeta and bleomycin whether administered simultaneously with these fibrotic triggers or a few days following the initiation of fibrosis, suggesting that E4, and other C-terminal endostatin polypeptides is also effective at reversing established fibrosis. The anti-fibrotic effects of E4 were noted whether it was administered intratracheally or intraperitoneally to mice in which pulmonary fibrosis was induced by bleomycin and dermal fibrosis was induced by TGFbeta. Furthermore, E4 exerted its anti-fibrotic effects via multiple pathways that include destabilization of ECM through reduction of LOX and thus decrease of ECM crosslinking, induction of ECM degradation via activation of MMP-2, suppression of Egr-1 levels, and induction of the TGFβ, thereby inhibiting transcription factor ID-1.

Thus, several in vitro assays and four in vivo and ex vivo pre-clinical models of fibrosis suggest that C-terminal endostatin polypeptides, as exemplified by E4, are an effective anti-fibrotic peptide that can block and reverse fibrosis in two organs, lung and skin. These anti-fibrotic effects as well as the lack of anti-angiogenic effects characteristic of endostatin render E4 an attractive therapeutic peptide for organ fibrosis.

It will be apparent that the precise details of the methods or compositions described may be varied or modified without departing from the spirit of the described invention. We claim all such modifications and variations that fall within the scope and spirit of the claims below.

The invention claimed is:

1. An isolated polypeptide comprising an endostatin polypeptide consisting of amino acids 145-153 of SEQ ID NO: 2 or SEQ ID NO: 13 fused to a heterologous peptide.

2. The isolated peptide of claim 1 wherein the heterologous peptide aids in detecting; purifying; stabilizing; or solubilizing the isolated polypeptide.

3. A pharmaceutical composition comprising an effective amount of the polypeptide of claim 1 and a pharmaceutically acceptable carrier.

4. A method of treating a subject with fibrosis, comprising selecting a subject with fibrosis; and administering to the subject a therapeutically effective amount of the polypeptide of claim 1, thereby treating the subject with fibrosis.

5. The method of claim 4, wherein the subject has a fibrosis of the skin.

6. The method of claim 4, wherein the subject has scleroderma, a keloid or hypertrophic scar, idiopathic pulmonary fibrosis, morphea, Graft-Versus-Host Disease, or subepithelial fibrosis.

7. The isolated polypeptide of claim 1, wherein the heterologous polypeptide is an immunoglobulin heavy chain constant domain or an immunoglobulin light chain constant domain.

8. The isolated polypeptide of claim 7, wherein the immunoglobulin light chain constant domain is a kappa light chain constant domain.

9. The isolated polypeptide of claim 7, wherein the immunoglobulin heavy chain constant domain is from IgG, IgA, IgE, IgD or IgM.

10. The isolated polypeptide of claim 9, wherein the immunoglobulin heavy chain constant domain is from $IgG_1$.

11. The isolated polypeptide of claim 1, wherein the heterologous peptide is an Fc domain.

12. The isolated polypeptide of claim 1, wherein the polypeptide is benzylated, glycosylated, acetylated, phosphorylated, myristoylated or pegylated.

13. The pharmaceutical composition of claim 3, formulated for intradermal administration.

14. The method of claim 4, wherein the polypeptide is administered intradermally to the subject.

* * * * *